US009029637B2

(12) United States Patent
Papes et al.

(10) Patent No.: US 9,029,637 B2
(45) Date of Patent: May 12, 2015

(54) CAMBIUM/XYLEM-PREFERRED PROMOTERS AND USES THEREOF

(75) Inventors: Fabio Papes, Campinas (BR); Isabel Rodrigues Gerhardt, Campinas (BR); Paulo Arruda, Campinas (BR)

(73) Assignee: Fibria Celulose S.A., Sao Paulo (BR)

( * ) Notice: Subject to any disclaimer, the term of this patent is extended or adjusted under 35 U.S.C. 154(b) by 1250 days.

(21) Appl. No.: 10/593,426

(22) PCT Filed: Mar. 28, 2005

(86) PCT No.: PCT/BR2005/000041
§ 371 (c)(1),
(2), (4) Date: Jun. 13, 2007

(87) PCT Pub. No.: WO2005/096805
PCT Pub. Date: Oct. 20, 2005

(65) Prior Publication Data

US 2008/0196125 A1 Aug. 14, 2008
US 2009/0229016 A2 Sep. 10, 2009

Related U.S. Application Data

(60) Provisional application No. 60/560,227, filed on Apr. 6, 2004.

(51) Int. Cl.
*C12N 15/82* (2006.01)
*A01H 5/10* (2006.01)

(52) U.S. Cl.
CPC ........ *C12N 15/8223* (2013.01); *C12N 15/8216* (2013.01); *C12N 15/8255* (2013.01); *C12N 15/8227* (2013.01)

(58) Field of Classification Search
CPC ........... C12N 15/8223; C12N 15/8227; C12N 15/8216; C12N 15/8255
USPC ........................................................ 800/287
See application file for complete search history.

(56) References Cited

U.S. PATENT DOCUMENTS

| 5,635,618 | A | 6/1997 | Capellades et al. | |
|---|---|---|---|---|
| 6,420,629 | B1 * | 7/2002 | Xue et al. | 800/284 |
| 7,365,186 | B2 * | 4/2008 | Phillips et al. | 536/24.1 |
| 2002/0124281 | A1 * | 9/2002 | Chiang et al. | 800/278 |
| 2003/0163837 | A1 | 8/2003 | Aldwinckle et al. | |

FOREIGN PATENT DOCUMENTS

| WO | WO 93/24638 A1 | 12/1993 |
|---|---|---|
| WO | WO 95/23230 A1 | 8/1995 |
| WO | WO 99/09188 | 2/1999 |
| WO | WO 00/56897 A1 | 9/2000 |
| WO | WO 00/71760 A1 | 11/2000 |
| WO | WO 00/78975 A2 | 12/2000 |
| WO | WO 01/95702 A1 | 12/2001 |
| WO | WO 02/20812 A1 | 3/2002 |
| WO | WO 02/50294 A1 | 6/2002 |

OTHER PUBLICATIONS

Kim et al. 1994, Plant Molecular Biology 24: 105-117.*
Fourgoux-Nicol et al. 1999, Plant Molecular Biology 40 :857-872.*
David Gordon et al., "Consed: A Graphical Tool for Sequence Finishing", Genome Research, 1998, pp. 195-202.
Stephen F. Altschul et al., "Gapped BLAST and PSI-BLAST: a new generation of protein database search programs", Nucleic Acids Research, 1997, vol. 25, No. 17, pp. 3389-3402.
J. Gielen et al., "The complete nucleotide sequence of the TL-DNA of the *Agrobacterium tumefaciens* plasmid pTiAch5", The EMBO Journal vol. 3, No. 4, pp. 835-846, 1984.
A. Depicker et al., "Nopaline Synthase: Transcript Mapping and DNA Sequence", Journal of Molecular and Applied Genetics, 561-573, 1982.
Richard A. Jefferson et al., "The GUS gene fusion system", Plant Molecular Biology Manual B14: 1-33, 1991.
F. Guerineau et al., "Sulfonamide resistance gene for plant transformation", Plant Molecular Biology 15: 127-136, 1990.
David M. Stalker et al., "Herbicide Resistance in Transgenic Plants Expressing a Bacterial Detoxification Gene", Science, vol. 242, Oct. 21, 1988, pp. 419-423.
Dilip M. Shah et al., "Engineering Herbicide Tolerance in Transgenic Plants", Science, vol. 233, pp. 478-481, Jul. 25, 1986.
M. De Block et al., "Engineering herbicide resistance in plants by expression of a detoxifying enzyme", The EMBO Journal vol. 6 No. 9, pp. 2513-2518, 1987.
Robert T. Fraley et al., "Expression of bacterial genes in plant cells", Proc. Natl. Acad. Sci. USA, vol. 80, pp. 4803-4807, Aug. 1983.
T.M. Klein et al., "High-velocity microprojectiles for delivering nucleic acids into living cells", Nature, vol. 327, May 7, 1987, pp. 70-73.
S.L. Beaucage et al., "Deoxynucleoside Phosphoramidites—A New Class of Key Intermediates for Deoxypolynucleotide Synthesis", Tetrahedron Letters, vol. 22, No. 20, pp. 1859-1862, 1981.
M.D. Matteucci et al., "Synthesis of Deoxyoligonucleotides on a Polymer Support", J. Am. Chem. Soc. 1981, 103, 3185-3191.
Xiaoqiu Huang et al., "CAP3: A DNA Sequence Assembly Program", Genome Research, 9:868-877, 1999.
Jane Aldrich et al., "RAPD Analysis in Flax: Optimization of Yield and Reproducibility using KlenTaq 1 DNA Polymerase, Chelex 100, and Gel Purification of Genomic DNA", Plant Molecular Biology Reporter vol. 11(2) 1993, pp. 128-141.

(Continued)

*Primary Examiner* — Li Zheng
(74) *Attorney, Agent, or Firm* — Arent Fox LLP

(57) ABSTRACT

The present invention relates to nucleic acid molecules corresponding to regulatory portions of genes whose expression is predominant in cambium and/or xylem. The invention also relates to compositions and methods of using the same to regulate the expression, in a cambium/xylem-preferred manner, of genes and/or any kind of nucleotide sequences in a plant. Nucleic acid molecules and its compositions include novel nucleotide sequences for cambium/xylem-preferred promoters identified and isolated from poplar (*Populus* spp). Methods for expressing genes and/or any kind of nucleotide sequences in a plant using the promoter sequences disclosed herein are provided. The methods comprise stably incorporating into the genome of a plant cell a nucleotide sequence operably linked to a cambium/xylem-preferred promoter of the present invention and regenerating a stably transformed plant that expresses the nucleotide sequence.

26 Claims, 5 Drawing Sheets

(56) References Cited

OTHER PUBLICATIONS

Nicole Bechtold et al., "In planta *Agrobacterium* mediated gene transfer by infiltration of adult *Arabidopsis thaliana* plants", Life Sciences 1993, 316: 1194-1199.
Csaba Koncz et al., "The promoter of TL-DNA gene 5 controls the tissue-specific expression of chimaeric genes carried by a novel type of *Agrobacterium* binary vector", Mol Gen Genet (1986) 204: 383-396.
Charles J. Thompson et al., "Characterization of the herbicide-resistance gene bar from *Streptomyces hygroscopicus*", The EMBO Journal, vol. 6, No. 9, pp. 2519-2523, 1987.
Richard A. Jefferson, "Assaying Chimeric Genes in Plants: the GUS Gene Fusion System", Plant Molecular Biology Reporter, vol. 5, No. 4, 1987, pp. 387-405.
Supplementary European Search Report EP 05 71 4408 dated Jun. 21, 2010.
Luguang Wu et al., "A xylem-specific cellulose synthase gene from aspen (*Populus tremuloides*) is responsive to mechanical stress", The Plant Journal (2000) 22(6), pp. 495-502.
Ann-Marie Johansson et al., "Characterization of a *PttRPS18* promoter active in the vascular cambium region of hybrid aspen", Plant Molecular Biology 52; 317-329, 2003.
Cuiying Chen et al., "Cell-Specific and Conditional Expression of Caffeoyl-Coenzyme A-3-O-Methyltransferase in Poplar", Plant Physiology, Jul. 2000, vol. 123, pp. 853-867.
Y. Shi et al., "Use of the rice sucrose synthase-1 promoter to direct phloem-specific expression of β-glucuronidase and snowdrop lectin genes in transgenic tobacco plants", Journal of Experimental Biology, vol. 45, No. 274, pp. 623-631, May 1994.
A. Dejardin et al., "Expressed Sequence Tags from Poplar Wood Tissues—A Comparative Analysis from Multiple Libraries", Plant Biology 6 (2004) 55-64.
N.S. Yang et al., "Maize sucrose synthase-1 promoter directs phloem cell-specific expression of *Gus* gene in transgenic tobacco plants", Proc. Natl. Acad. Sci. USA, vol. 87, pp. 4144-4148, Jun. 1990.
"M122F06 Populus flower cDNA library *Populus balsamifera* subsp. trichocarpa cDNA 5 prime, mRNA sequence.", sequence, retrieved from EBI accession No. EMBL:BU868822, 2002.
"MTU6CR.P7.F05 Aspen root cDNA Library *Populus tremuloides* cDNA, mRNA sequence." sequence, retrieved from EBI accession No. EMBL:CA927326, 2002.
"MTU6TR.P15.G10 Aspen root cDNA Library *Populus tremuloides* cDNA, mRNA sequence." sequence, retrieved from EBI accession No. EMBL:CA928021, 2002.
"ORNL031 Poplar BAC Library *Populus balsamifera* subsp. trichocarpa genomic similar to Enzyme, DNA sequence.", sequence, retrieved from EBI accession No. EMBL:BH860560, 2002.
"*Populus balsamifera* subsp. trichocarpa cad gene for cinnamyl alcohol dehydrogenase, exons 1-5", sequence, retrieved from EBI accession No. EMBL:AJ295837, 2000.
"*Populus balsamifera* subsp. trichocarpa ccr gene for cinnamoyl-CoA reductase, exons 1-5", sequence, retrived from EBI accession No. EMBL:AJ295838, 2000.
"*Populus kitakamiensis* (*P. sieboldii* X *P. grandidentata*) homt1 gene for caffeic acid O-methyltransferase, complete cds (exonl-4).", sequence, retrieved from EBI accession No. EMBL:D49710, 1995.
"*Populus kitakamiensis* cyp73a gene for cinnamic acid 4-hydroxylase, complete cds.", sequence, retrieved from EBI accession No. EMBL:D82812, 1995.
"*Populus kitakamiensis* cyp73b gene for cinnamic acid 4-hydroxylase, partial cds." sequence, retrieved from EBI accession No. EMBL:D82813, 1995.
"*Populus tremuloides* caffeic acid/5-hydroxyferulic acid O-methyltransferase (PTOMT1) gene, complete cds", sequence, retrieved from EBI accession No. EMBL:U13171, 1994.
"PtaXM0014C6C0606 Poplar cDNA library from mature xylem *Populus x canescens* cDNA 5', mRNA sequence.", sequence, retrieved from EBI accession No. EMBL:CF228540, 2003.

"xylem.est.507 Poplar xylem Lambda ZAPII library *Populus trichocarpa* cDNA 5', mRNA sequence.", sequence, retrieved from EBI accession No. EMBL:A1166701, 1998.
Baucher et al., "Molecular Tools to Study Lignin Biosynthesis in Poplar", Med. Fac. Landbouww. Univ. Gent. 1997, pp. 1403-1411, vol. 62, No. 4a.
Bell-Lelong et al., "Cinnamate-4-Hydroxylase Expression in *Arabidopsis*", Plant Physiology, 1997, pp. 729-738, vol. 113.
Boudet et al., "Tansley Review No. 80 Biochemistry and molecular biology of lignification", New Phytology, 1995, pp. 203-236, vol. 129.
Buhtz et al., "Xylem sap protein composition is conserved among different plant species", Planta, 2004, pp. 610-618, vol. 219.
Canevascini et al., "Tissue-Specific Expression and Promoter Analysis of the Tobacco Itp1 Gene", Plant Physiology, 1996, pp. 513-524, vol. 112.
Capellades et al., "The maize caffeic acid O-methyltransferase gene promoter is active in transgenic tobacco and maize plant tissues", Plant Molecular Biology, 1996, pp. 307-322, vol. 31.
Chaffey et al., "A cytoskeletal basis for wood formation in angiosperm trees: the involvement of cortical microtubules", Planta, 1999, pp. 19-30, vol. 208.
Chaffey et al., "Myosin, microtubules, and microfilaments: co-operation between cytoskeletal components during cambial cell division and secondary vascular differentiation in trees", Planta, 2002, pp. 526-536, vol. 214.
Dalessandro et al., "Changes in Enzymic Activities of Nucleoside Diphosphate Sugar Interconversions during Differentiation of Cambium to Xylem in Pine and Fir", The Biochemical Journal, 1977, pp. 281-288, vol. 162.
Dalessandro et al., "Changes in Enzymic Activities of Nucleoside Diphosphate Sugar Interconversions during Differentiation of Cambium to Xylem in Sycamore and Poplar", The Biochemical Journal, 1977, pp. 267-279, vol. 162.
European Search Report, dated Apr. 26, 2013, issued in European Patent Applcation No. 12192001.1.
European Search Report, dated Apr. 26, 2013, issued in European Patent Application No. 12191998.9.
European Search Report, dated Apr. 29, 2013, issued in European Patent Application No. 12192005.2.
European Search Report, dated Feb. 14, 2013, issued in European Patent Application No. 12191983.1.
European Search Report, dated Feb. 18, 2013, issued in European Patent Application No. 12191980.7.
European Search Report, dated Feb. 18, 2013, issued in European Patent Application No. 12192016.9.
European Search Report, dated Feb. 22, 2013, issued in European Patent Application No. 12191986.4.
European Search Report, dated Jan. 16, 2013, issued in European Patent Application No. 12192008.6.
European Search Report, dated Mar. 25, 2013, issued in European Patent Application No. 12191992.2.
European Search Report, dated May 8, 2013, issued in European Patent Application No. 12192011.0.
European Search Report, dated May 8, 2013, issued in European Patent Application No. 12192012.8.
Feuillet et al., "Tissue- and cell-specific expression of a cinnamyl alcohol dehydrogenase promoter in transgenic poplar plants", Plant Molecular Biology, 1995, pp. 651-667, vol. 27.
Franke et al., "Modified lignin in tobacco and poplar plants overexpressing the *Arabidopsis* gene encoding ferulate 5-hydroxylase", The Plant Journal, 2000, pp. 223-234, vol. 22, No. 3.
Guan et al., "ag13 is expressed in *Alnus glutinosa* nodules in infected cells during endosymbiont degradation and in the nodule pericycle", Physiologia Plantarum, 1997, pp. 601-607, vol. 99.
Guan et al., "Gene expression in ineffective actinorhizal nodules of *Alnus glutinosa*", Acta Botanica Gallica, 1996, pp. 613-620, vol. 143, No. 7.
Guiderdoni et al., "Inducibility by pathogen attack and developmental regulation of the rice Ltp1 gene", Plant Molecular Biology, 2002, pp. 683-699, vol. 49.
Harper et al., "Biosynthesis of UDP-Xylose. Cloning and Characterization of a Novel *Arabidopsis* Gene Family, UXS, Encoding Soluble

(56) References Cited

OTHER PUBLICATIONS and Putative Membrane-Bound UDP-Glucuronic Acid Decarboxylase Isoforms", Plant Physiology, 2002, pp. 2188-2198, vol. 130.

Hawkins et al., "Characterisation of caffeic acid O-methyltransferase and cinnamyl alcohol dehydrogenase gene expression patterns by in situ hybridisation in *Eucalyptus gunnii* Hook. plantlets", Plant Science, 2003, pp. 165-173, vol. 164.

Hawkins et al., "Cinnamyl Alcohol Dehydrogenase: Identification of New Sites of Promoter Activity in Transgenic Poplar", Plant Physiology, 1997, pp. 321-325, vol. 113.

Hayakawa et al., "Molecular cloning and tissue-specific expression of two genes that encode caffeic acid O-methyltransferases from *Populus* kitakamiensis", Plant Science, 1996, pp. 157-165, vol. 113.

Horvath et al., "Expression Analysis of a Family of nsLTP Genes Tissue Specifically Expressed throughout the Plant and during Potato Tuber Life Cycle", Plant Physiology, 2002, pp. 1494-1506, vol. 129.

Humphreys et al., "Rewriting the lignin roadmap", Current Opinion in Plant Biology, 2002, pp. 224-229, vol. 5.

Huntley et al., "Significant Increases in Pulping Efficiency in C4H-F5H-Transformed Poplars:Improved Chemical Savings and Reduced Environmental Toxins", Journal of Agricultural and Food Chemistry, 2003, pp. 6178-6183, vol. 51. No. 21.

Kawai et al., "Isolation and Analysis of Cinnamic Acid 4-Hydroxylase Homologous Genes from a Hybrid Aspen, *Populus kitakamiensis*", Bioscience Biotechnology Biochemistry, 1996, pp. 1586-1597, vol. 60, No. 10.

Kobayashi et al., "Purification and cDNA Cloning of UDP-D-Glucuronate Carboxy-lyase (UDP-D-xylose Synthase) from Pea Seedlings", Plant Cell Physiology, 2002, pp. 1259-1265, vol. 43, No. 11.

Lacombe et al., "Characterization of cis-elements required for vascular expression of the Cinnamoyl CoA Reductase gene and for protein-DNA complex formation", The Plant Journal, 2000, pp. 663-676, vol. 23, No. 5.

Lauvergeat et al., "The vascular expression pattern directed by the *Eucalyptus gunnii* cinnamyl alcohol dehydrogenase EgCAD2 promoter is conserved among woody and herbaceous plant species", Plant Molecular Biology, 2002, pp. 497-509, vol. 50.

Li et al., "The Last Step of Syringyl Monolignol Biosynthesis in Angiosperms is Regulated by a Novel Gene Encoding Sinapyl Alcohol Dehydrogenase", The Plant Cell, 2001, pp. 1567-1585, vol. 13.

Loopstra et al., "Purification and cloning of an arabinogalactan-protein from xylem of loblolly pine", Planta, 2000, pp. 686-689, vol. 210.

Loopstra et al., "Xylem-specific gene expression in loblolly pine", Plant Molecular Biology, 1995, pp. 277-291, vol. 27.

Lu et al., "Regulatory sequences distinguish the physiological function of multiple cinnamate 4-hydroxylase genes in quaking aspen", abstract, Plant Biology, 2003.

Meng et al., "Substrate profiles and expression of caffeoyl coenzyme A and caffeic acid O-methyltransferases in secondary xylem of aspen during seasonal development", Plant Molecular Biology, 1998, p. 513-520, vol. 38.

Meyer et al., "Ferulate-5-hydroxylase from *Arabidopsis thaliana* defines a new family of cytochrome P450-dependent monooxygenases", Proceedings of the National Academy of Sciences, 1996, pp. 6869-6874, vol. 93.

Meyer et al., "Lignin monomer composition is determined by the expression of a cytochrome P450-dependant monooxygenase in *Arabidopsis*", Proceedings of the National Academy of Sciences, 1998, pp. 6619-6623, vol. 95. No. 12.

Mizutani et al., "Isolation of a cDNA and a Genomic Clone Encoding Cinnamate 4-Hydroxylase from *Arabidopsis* and Its Expression Manner in Planta", Plant Physiology, 1997, pp. 755-763, vol. 113.

Nair et al., "The *Arabidopsis thaliana* Reduced Epidermal Fluorescence1 Gene Encodes an Aldehyde Dehydrogenase Involved in Ferulic and Sinapic Acid Biosynthesis", The Plant Cell, 2004, pp. 544-554, vol. 16.

No et al., "Sequences upstream and downstream of two xylem-specific pine genes influence their expression", Plant Science, 2000, pp. 77-86, vol. 160, No. 1.

Rep et al., "A tomato xylem sap protein represents a new family of small cysteine-rich proteins with structural similarity to lipid transfer proteins", FEBS Letters, 2003, pp. 82-86, vol. 534.

Rigau et al., "Analysis of a maize α-tubulin gene promoter by transient expression and in transgenic tobacco plants", The Plant Journal, 1993, pp. 1043-1050; vol. 4.

Ro et al., "Functional Characterization and Subcellular Localization of Poplar (*Populus trichocarpa* x *Populus deltoides*) Cinnamate 4-Hydroxylase", Plant Physiology, 2001, pp. 317-329, vol. 126.

Ruegger et al., "Regulation of Ferulate-5-Hydroxylase Expression in *Arabidopsis* in the Context of Sinapate Ester Biosynthesis", Plant Physiology, 1999, pp. 101-110, vol. 119.

Sabala et al., "Tissue-specific expression of Pa18, a putative lipid transfer gene, during embryo development in Norway spruce (*Picea abies*)", Plant Molecular Biology, 2000, pp. 461-478, vol. 42.

Samaj et al., "Immunolocalization of cinnamyl alcohol dehydrogenase 2 (CAD 2) indicates a good correlation with cell-specific activity of CAD 2 promoter in transgenic poplar shoots", Planta, 1998, pp. 437-443, vol. 204.

Sarni et al., "Purification and properties of cinnamoyl-CoA reductase and cinnamyl alcohol dehydrogenase from poplar stems (*Populus X euramericana*)", European Journal of Biochemistry, 1984, pp. 259-265, vol. 139.

Showalter, A.M., "Arabinogalactan-proteins: structure, expression and function", CMLS Cellular and Molecular Life Sciences, 2001, pp. 1399-1417, vol. 58.

Sibout et al., "Expression of a poplar cDNA encoding a ferulate-5-hydroxylase/coniferaldehyde 5-hydroxylase increases S lignin deposition in *Arabidopsis thaliana*", Plant Physiology and Biochemistry, 2002, pp. 1087-1096, vol. 40.

Sibout et al., "Expression Pattern of Two Paralogs Encoding Cinnamyl Alcohol Dehydrogenases in *Arabidopsis*. Isolation and Characterization of the Corresponding Mutants", Plant Physiology, 2003, pp. 848-860, vol. 132.

Sohal et al., "The promoter of a *Brassica napus* lipid transfer protein gene is active in a range of tissues and stimulated by light and viral infection in transgenic *Arabidopsis*", Plant Molecular Biology, 1999, pp. 75-87, vol. 41.

Sterky et al., "Gene discovery in the wood-forming tissues of poplar: Analysis of 5,692 expressed sequence tags", Proceedings of the National Academy of Sciences, 1998, pp. 13330-13335, vol. 95.

Suzuki et al., "Cloning and expression of a UDP-glucuronic acid decarboxylase gene in rice", Journal of Experimental Botany, 2003, pp. 1997-1999, vol. 54, No. 389.

Tsai et al., "Nucleotide Sequence of a *Populus tremuloides* Gene Encoding Bispecific Caffeic Acid/5-Hydroxyferulic Acid O-Methyltransferase", Plant Physiology, American Society of Plant Biologist, 1995, p. 1459, vol. 107.

Uribe et al., "Maize α-tubulin genes are expressed according to specific patterns of cell differentiation", Plant Molecular Biology, 1998, pp. 1069-1078, vol. 37.

Vander Mijnsbrugge et al., "Wood formation in poplar: identification, characaterization, and seasonal variation of xylem proteins", Planta, 2000, pp. 589-598, vol. 210.

Wang et al., "Isolation and characterization of genes involved in vascular development in quaking aspen (*Populus tremuloides*)", abstract, Plant Biology, 2000.

Wei et al., "Cloning of cDNA Encoding Comt from Chinese White Poplar (*Populus tomentosa*), Sequence Analysis and Specific Expression", Acta Botanica Sinica, 2001, pp. 326-328, vol. 43, No. 3.

Wheatley et al., "Characterisation and immunolocation of an 87 kDa polypeptide associated with UDP-glucuronic acid decarboxylase activity from differentiating tobacco cells (*Nicotiana tabacum* L.)", Phytochemistry, 2002, pp. 771-780, vol. 61.

Yahiaoui et al., "Comparative Efficiency of Different Constructs for Down Regulation of Tobacco Cinnamyl Alcohol Dehydrogenase", Phytochemistry, 1998, pp. 295-306, vol. 49, No. 2.

(56) References Cited

OTHER PUBLICATIONS

Yubero-Serrano et al., "Identification of a strawberry gene encoding a non-specific lipid transfer protein that responds to ABA, wounding and cold stress", Journal of Experimental Botany, 2003, pp. 1865-1877, vol. 54, No. 389.

Zhang et al., "An arabinogalactan protein associated with secondary cell wall formation in differentiating xylem loblolly pine", Plant Molecular Biology, 2003, pp. 91-102, vol. 52.

Zhang et al., "Differential expression of genes encoding cell wall proteins in vascular tissues from vertical and bent loblolly pine trees", Tree Physiology, 2000, pp. 457-466, vol. 20.

\* cited by examiner

SEQUENCE LISTING

```
<160> NUMBER OF SEQ ID NOS: 41

<210> SEQ ID NO 1
<211> LENGTH: 3035
<212> TYPE: DNA
<213> ORGANISM: Populus sp.
<220> FEATURE:
<221> NAME/KEY: promoter
<222> LOCATION: 1)...(3035)
<223> OTHER INFORMATION: Sucrose synthase (SUSY) promoter

<400> SEQUENCE: 1
tcatgtccta tccaacggcg atgcaaactt cgctgtcccg cacttttca  taggacgagg      60 tgaagtttag ctatatatct tttttttta  atttaaattg ttaattcttt  atatttttat     120
attcttttaa ttttatattt  ttatattatt ttgatatatt acatcaagaa taaattttaa    180
aaaaataatt tttaaaattt  acttaaccac gcaatacata aaaaataata gaacccacca    240
acctaagaat acttgtcaat  gcatagaagt acacctgcta gttcttaaaa ccaacaaaag    300
gaagcaaagt agatctctga  gtcaaaaacc agaggaaacc atagaaacac ataataataa    360
taataataat aataataata aaattaattt  aacttggtgt aataataaaa ttaatttaat    420
tacaaagagt gtaactcaac tagtcatgtt ctaaatttat  tctctagaga ttactagttt    480
```

```
gagttttaca aatttttaagg ccactgaaga tttatatagt cattaatttc agaatatata    540
agattagttg agttacgtat aaattgatta aaaaatcata ttaataaaaa taaaaaaatt     600
aatttaaagg tttaagaaat caaattaaga gaaagagtg gtgttttatt tttcatcgtg      660
ccctctctca acagacaagt agaatgatga gagagagagg gtaaagaaat ggatttatga    720
gaacattgac cacagggaaa gagagaagcg gttttgtgaa aggaacaatg aaaccacagg    780
aaggtaaagc ggtaatgata tatttcacga atactaaaac tagaacaaca agttttttaa   840
tcaaattaaa ccacgagtgc aaggccgtct tctctgtgta taaaagggtc cttcttcttt   900
ctcatttccc attctcatct gcaaacttct cctttgcaat cttttctttct tgcgttctgt  960
gtgttcgttg tgatttgtgt tcattcttct tgtctattag cttgtccccc cgtccgactg   1020
ctttctgtat ttattctggc attaagctta aggtaaagat ccctcaacta tcccaagcaa   1080
tttattctgt ttttatgtga tcttgaggga tcttcctctt ggatgcgctt tttatttttt    1140
cttcctcctt cttcctgctc cttcttacct tgtatctgat cccccagacg aaaatgtttt   1200
ttgttttttt aattagctca acaaatcaaa aacattcaca taataacaca gctcgaaaga   1260
aatctgatac agttttaatc tgttgtattt taaaaatcat tacagttcat gcatgctgat   1320
actttaccat gtcatgaaat taaatcccag catcctttc catagccaaa gaaggatcag    1380
cagcatgctg atagtttacc atgtcatgaa attaaatccc agcatccttt tccatagcca   1440
aagaaagatc agcagcatgc ttgcttatac aaggtcttcg cttgcttatc aaggccactg   1500
aaacatcatc atcgtcataa ctatgataga acccgcctac tgccggcatt gaaaacatca   1560
tcactagtgt ctctacatta aaaaacaccc actgtcaat tcctattttt tttactctta    1620
aaatgtcttt cggcttgagc tcctcgggct ccacggatgg caactgctgt attatatata   1680
tatatatata tatatatata tatatatata tatatatata tatatatata tatatttccc    1740
tgttggctac atagacctgt taataccgta taaatagata atattaatat atagaattca   1800
tgtatctttc cgagattaag cgatgccgta taaataatat taatatcttt gaatcagtat   1860
gtatattaat taaaattaat ttttttcaaa gtaatttaa gagcgcattt tcaacatcca    1920
tttagttttt ttttaataat aaatctctct ttgcattaat cctaacgttt gaacttagta   1980
aattaaaaaa aggaaaatac cttttttcacc aatatagaat caatgaacag cactagtttg  2040
cttgaaataa aaataaaaat aaaatctaat aagacatttc gaaatcatcc ttatccgcaa   2100
atcactacat tagtatagta tcttgaaaga taagcaagga tcatgcaagt ttataataat   2160
taaacttaaa acgtactatg acgtgtgcat cattcattca ttctgcatga aactctccac   2220
aagtctagcc tttgcatcat tcattctact tcattttatt ttttcctcta atggtttcga   2280
ttgatttttc tttcttagag tctggtcttt tagttcaact ttacatgttt taggctcgta   2340
ttttgagaga aaaaaagaa aaaagtatgc agatcatgat tctgcaaaat actgaactag    2400
tgttctgatg aattaacatg tagcatgtat aatgctggaa gaactaaaga gcagttgggc   2460
tgccatgacc aaaagaaact tcgactgatt ataaatgtca aaacttgggc ccattctttg   2520
gtttctgtct gttgttttat gccatggcaa aactctgctt atttttcaac gtccaacgtc   2580
aaatgggaga ggtttaaatt ctattgttat gtctaaacca cgtggttgtt atctatatct   2640
gaccgaacat tcaagctttt ggtattccac aagaagggtt ttctctcttc tttcttttca   2700
taattgtaat gtgtttaatt tgtttcttgc ccaataatct tctctgcttc aaactaactt    2760
taattgttcg atctcttgcg ttatttttaga catgtgcaat cacctttcac tgttgaaaaa   2820
atggttggtg aggtgaggtg gtaggttttg aagtcttcta gaataatgtg gtttctctgt   2880
```

```
tgctcttgac ttcttcttgt agatcatttc tggctggcta agctatccat acccccccgc    2940
ccctacaaat aatattgagt tgttgctggt cttaattcct attatctgtt attactccca    3000
ctgattgctt tctgtttctc ttaaggagct atggc                               3035
```

<210> SEQ ID NO 2
<211> LENGTH: 2513
<212> TYPE: DNA
<213> ORGANISM: Populus sp.
<220> FEATURE:
<221> NAME/KEY: promoter
<222> LOCATION: (1)...(2513)
<223> OTHER INFORMATION: alpha-tubulin (TUB) promoter

<400> SEQUENCE: 2

```
ccctggaggt tggggtgagt gaaataagag ggttaaatat ttttttttgga ttaaaccatt      60 caaagtgaat tttttaataa aatctcatag gctgattaaa tgaaattcct ttagagtcat     120
catacggtaa atttgatgtt agtttggtgt tatagtgcaa attactttt aattaaaaga      180 tagcaatgct tccagcatgg tggactcgtt tttcaaatcg aaagctgctt cttcttcttt     240
gttttttttt tttaatcttg ttttttctaat ttcataaaaa ccaatcatta tttcgcaggt    300
caggtagtta aatttgttag gctaattgat ccagaaacct ccggaaagtc aaactcaaat    360
aaactgctga ccttttttatt tatttttatt ttttgaattc taattcgtcg gactatctgg    420
tcaagataat ccacctctca tgcgaatact tcttagagtg ccatccatta taccctgtta    480
agttgccggt gattgcacat gtttgaccac cctccctccc ctaattttca cggcggaaag    540
gggcttgttt gggcttgttt taaattataa aatagtgat gatttaaagt atttttatt      600 taaaatata ttaaaataat tttttttatt tttaaaat tatttttaac atcaaaacaa       660
catgaaaaca taaaaaaatt gttttcattc tttttaaaaa tattttttt ctattttat     720 tcaatattat tatatagttt tcttattttt atttttctat taagtattat taggtttttc    780 tgttttttt tttaatttaa aggaaataat tttttttta ttcaatatta ttagaaattt     840 ctaattttt ctatataaag gattttaaaa ttgtaataac attttgacaa gaaatttaat    900
gaataaaaat taaatattct agatatctct tcacagttat gacattcttg gttttaattt    960
ataataaatc gcattatcat taaccctcgg ctaaattatc tatttattta tgaccatgga   1020
aacacaagtg cgtgtgtatt tggggaggtg tgggttaaa gcctgcaata taattgaaga    1080
aaaaatttaa gaatttttcc gcgttgatga aaccctgatt gaaggttgga gcatgcctca   1140
ataggcagac gggcgaaact tagaaaccag gaataaacgt gaaacacggg attcacacga   1200
atttggaaat ccacgcttgt aaagaaaacc aaaccgcata attttatttc ctatttgttt    1260
tcgcgtcttg ttttaaaaa atttaaattt tattttattt tttttttctttt aaattaatat  1320 ttttttgata attttagatc attttaatat gctgatatca aaataaaatt ttaaaaaata   1380
aaaaaaatat attattttaa tatatttcta aataaaaaac acttcaaaaa acaattataa    1440
ccatattttc aaacaagtac tattaaaaaa gtgatggaca agagaaatca aggggtcgcg   1500
gatgcgcttc agcaatagtg aatgacaact agtctaaagt taaaacttag acctcctcgc   1560
gtaaatttta tatttatat tttaatatta atacattaaa ataattaaaa aataattaa     1620 aaatcattaa ttcatacaaa attttttaaag catattaaaa agagaataaa cggcaaaaac   1680
aaacctacgc taattgtgaa ataaaagatt aatctatgca cacggtatcg ttttacttca   1740
ctggtcggtg taataatttc tctaaccttta tgacccaaca attcactatt ttgaaaccct   1800
```

-continued

| | |
|---|---|
| tgttattatt tttttatca accatttct taatctccat ttcactcatt ccagttgcct | 1860 |
| ggacagtgga catggtggcg gtgcctcttg atcttttcta gttgggccac atgaatacac | 1920 |
| ttcaagggat ttgaaactag gcctaatcga ttgaaacgta aatccactc tctaattgag | 1980 |
| aggacggccc accctcctgg cgacgtgcc ctctcatcca ccaggaccac cgccatcatg | 2040 |
| ccttctctgc tccttcctca cgcctcccaa cagaatgaca ttattagcct ccatcccaac | 2100 |
| tatagaccgg cagtggcaca actgcaattt cctacaaccc aagacgatcc ccaaaactaa | 2160 |
| attcaaaaat caaaatggag cgggcaacta accatggtta aaataacgat tcggccaacc | 2220 |
| tggcaaaatc aagaattagg tggcttggga acggcatca ttggcatgca cctaatttga | 2280 |
| cccgtggtta aactaaccct ggttagctaa accacacact ccctccgtcc cctaatttct | 2340 |
| ctccctctga agtatataaa accccatact cacagaccta aagctcacc cctgaaattt | 2400 |
| cataggcgtc ttgataaacg ccaccctccc tcagcatcaa ttccaattgt ctttgctttc | 2460 |
| gattttctct tcttttaata tctgttgatc tttgtgcttt gagagaaaat gag | 2513 |

<210> SEQ ID NO 3
<211> LENGTH: 2041
<212> TYPE: DNA
<213> ORGANISM: Populus sp.
<220> FEATURE:
<221> NAME/KEY: promoter
<222> LOCATION: 1)...(2041)
<223> OTHER INFORMATION: Arabinogalactan protein (ARAB) promoter

<400> SEQUENCE: 3

| | |
|---|---|
| caaaggatca tggagttgga atccccacca tccctatttt atttgataaa aattaagcac | 60 |
| cagggtggta gggatctatg caagttccaa gttcaaagga cttttcactg gaagtgatat | 120 |
| gtcagagaat aatatataaa ttatttcttg gaatctcacc aatccctatt tatttgataa | 180 |
| aaattaagta caaggtagtg cgaaacctgt acaagttta agcctaaagg ctttcactt | 240 |
| gaagaggtgt gttagagaat aatataaatc atatcttaga accttaccta acatcttaag | 300 |
| ctattgagat gagatgattc tttgacatgg tatcagaact ttaatgacca aacagtcatg | 360 |
| agtttgaatc tcaccatccc tatttatttg ataaaaatta agcacaagat agtgtgggca | 420 |
| tgtgcaagtt tcaagcttaa ttgactttta cttgaggggt gtgtgttaga gaatgatata | 480 |
| aatcatatct tggaatctta cctaataact aagttattg gattgagatg attatttgac | 540 |
| gatcagagaa gacaaagcat gcattaagga gggtagagag aaaggaaaag gaggttgcag | 600 |
| gacaatggtg aaagcaaata tttcattaca agttttgaa gtggttggaa tcaaaatgtt | 660 |
| gttctcttta atctgtaaga ttatatatgg ttctgctgac aacatttgaa tgcgaggctg | 720 |
| aacataatgc aaaagagtag aaaatgctaa ttatcaagaa atcaggcttc tgaaacagaa | 780 |
| ctacctttac taggttatct cttgaacttc tactaaactt aatgtgaaca aatctgctgt | 840 |
| attgctctca cacaggaacc ttttaagttt cctcagaatg aatttttctc tagtttaagc | 900 |
| aatcccacat caggttaagt tctttttctcc tgtttcaaaa ctgctggtgt tgataattag | 960 |
| agaaaagaga gtgttagaga gcataggatt gttactttaa gcttgaggaa gtggattcca | 1020 |
| atcagtaaaa ttgtcgaggt tatatcacaa ttttcataaa ctgaatgtga cagacgactg | 1080 |
| ccagaaaaac ccttctatga tttgctgcat tatggaggaa aatcatggtt ttggtggaag | 1140 |
| catgatccat tcatcctagt acgtttaaca tgaataaaag gcttgagctc tagtacagaa | 1200 |
| tcccttgcct caactccctt catccttcct cctccgcgtt catctacaaa accctcctcc | 1260 |
| accgcctttt ctttcatcct ctccatgaat aaaagactat tatgccattc aacatcatgt | 1320 |

```
aaaagaacac aattcctttt acttcgaaat ggctatctta aagtttcaag acttgcgttt    1380
gcatactgca aaatcacttt tatcaatagc atgacctcac cgggctcatg tacataaggt    1440
aagtgtttct tcatgaagtt gtgttaagtg atggtctggt gtgagatttg atttctgagc    1500
gtgcgaatct agaaaattag tgatctatca atgtctgtca aggattaagg atgtaaatat    1560
tcgttctttt aagctaaaag agcaaagact tggctattta cgatacaaag gtcagtttag    1620
atcgcttgtc taaatcttct gtcattatag atgatttgtt ttgatgttaa gaagcatgct    1680
cagctgttct gctagtgatg attcacaatc atggacatct ttatttgttg tcacagccac    1740
ttgaaatcta cctttttagaa cctttttttt ttgcctgctt ttccaaggaa agtagttgct    1800
gcagcattgt taaatttccc tctccattga tgaccctaca gcttttggag tgagataagg    1860
tactagcaat ctagttgtat aactaaaatt gtatattgca cctaacttga tcctctgtcc    1920
actactataa aaacctcact ctatctcatc tttacacatc aaacacttta tgattgaaat    1980
caatttgcat tagtatattt gaattgtttc gagcatttta tcccaaaaaa ataaggatga    2040
a                                                                   2041
```

<210> SEQ ID NO 4
<211> LENGTH: 2422
<212> TYPE: DNA
<213> ORGANISM: Populus sp.
<220> FEATURE:
<221> NAME/KEY: promoter
<222> LOCATION: 1)...(2422)
<223> OTHER INFORMATION: Caffeic acid 3-O-methyltransferase (COMT)
      promoter

<400> SEQUENCE: 4

```
cataatatca aaacttaagc agatcaaatt gaaatatatt tgtaatttttt atataaatta     60 gcactgatat gtcaaaataa agacttcaaa ttcaaaactt aagtagacca aactgaaata    120
tatttgtaat tcctatagaa atcaacattg gtataccaaa ataagagtt tagatttctg     180 atctagcctg cagcagcaga gtaaaacaaa aataaagtct gaataggaat cacgaaataa    240
aatgaaatga agaattgcaa aatcataatt aaatgaagtc tgaagtttca aaatcctgac    300
caggtataaa attaagatgc aaaaaacaaa atcttatcag aactaaagtt agataatcga    360
aagtaaagta gaatctagat ttaattaatg tattggaggg gaacaattgt tcatattcga    420
tcaaggaaat taacacctaa ttaaataaaa aggctcgaag atgagaagga cggtgcatgg    480
atggtcaaaa aacgaagcag cagaagagaa tggtcggtgg tgcacagtca tgttaaatgt    540
ccaaattaaa aacaaaaaaa aggtttaatt atgaaaatat ttcattctta acgaatatat    600
caaactgcca aaccccccac cggttccatt tatatgggag gagtgattga tattttttatt    660 aaactcaatt tatttataat ttaatttaaa atctgattga tgtcttataa taaattttaa    720
aaaaatatat agataaaggt tgatctagtc aattcaagag tcaataatga ttttatcaaa    780
atttaattta attttttaa aaacaaaaca taattccaaa acaatgttgt ttggatttt     840 ttttttaaaaa aaaacataat ccacccatgt cattaattta ccaaactcct aacacaatca    900
tgtttaataa cccttcaatt ttcaaaaata atttcagttc ttatatttat ttttatttgc    960
aaattagtcc ttgtttgaat tttctttta gttcttatac tttacaaaaa ttatagttta   1020 ttttttatt gtgattcttt ttattataat taaggtccct acatgctttt tttttatgt   1080 aatgcttttt aatgtaataa atcattctga ttgtaatcat caattatata attatttga   1140 caattacata attaaatata gaaatataat aaattattac gttacatgat ctattactaa   1200
```

```
gtacccaagt ctctacgtca atgttcaatt ttcagcaggt ggttctgtta gaatgtccca    1260
tccaaaatat ggattcattg atacgatttt taagtccaaa caaccctcat attaagcaaa    1320
accctcatat taagcaaaag attattatta ttattattat tattattatt tattattatt    1380
attattgttt ttgttgttgt gcttcttctt tttctcaatc aacaaaattt ttaccaactt    1440
caagattttt ttttttatgg ttaaaggtat actaatatga cctaataact tagaagtgtg    1500
gattatagat aaaattagca attcgtgcta tatagtgggt tggatattta tttatataaa    1560
aaaattatat ataagttttt ttttttatgc atacttgtac aaaaaaaaaa tataaataca    1620
aatcaaatat ttattcaatc aaatgataat agaaccagat atatgaaaa ttgattaaaa     1680 aaaatatatc atgttaggtc aacatattag aaatactata caaaaataaa tatttatatg    1740
tatataacac atacaaagat tttctatagc gtgtgtttat tcagtgagtt tcatttatat    1800
taactttaaa atcattagtt ttataggatg taaatttatc ttttattaat tttaaatgtg    1860
ttcaataaat acaatcgggt gaatgtatca ttatgtgatt gaatatctta atctgcattt    1920
atctcttaat tttttcagtt ttttttttgt tattgttaat gaatttttt ttatttatat     1980 aaatgattat tgatttattt aattagatgc tttatacttt aattttttat atataaaaaa    2040
acatattaaa acaatctata tacctgatat tttattttt aaaaattata acccatgata     2100
aagaagtttt ataaacctac ctgcttgaca tattacatca tgttccaata gtctcccctg    2160
aaacaggtta aaaaaaaaa agtttggcaa ataagacgag gaaaaatata tagaaaaaaa     2220
ggtagggagt cagttctagg aagaagacat tgtgcatca agtagagagg agggaccaac     2280
cacaaggtgg ttgagcactt caccatatat agcaccactt tgcaacctct ttttcagtat    2340
tctcatatcc tcttcacttc ttttcttttc accttcttca acctttttgtt tccttaaaga   2400 attcaatctt gatcaagatg gg                                             2422
```

<210> SEQ ID NO 5
<211> LENGTH: 793
<212> TYPE: DNA
<213> ORGANISM: Populus sp.
<220> FEATURE:
<221> NAME/KEY: promoter
<222> LOCATION: (1)...(793)
<223> OTHER INFORMATION: cinnamyl alcohol dehydrogenase (CAD) promoter

<400> SEQUENCE: 5

```
ttgaattgat gacgtaggaa acatgataaa catgtaatct aaatatatct catgtctagg      60
tcatgggttt cacgtattag tccagcttta tccaaaataa ttttttttatt tgttattatt    120 gttaccttat tttttcatca tattattaaa ttaattaaaa tttaatcaaa acattaattt    180
tttcttactt ttttttaaaa tataatcttc tcttaaattt ctttttttcat gtttaaaaaa    240 atttcagtcg acggcacaac aatccagtaa ataccaaggg tatattgtcg ccactcacca    300
ccaactacgt caattaagca aataatataa ttaggcaact gtgtaaccac catggaaatt    360
aagatattcc tttcatgaaa tacttaatta gtgacgtata catgatgctc caaacctcat    420
cacagattca gtgttcttaa ctattatgtt ccctttttgtt tcccaagaac catgagttaa    480
tcaggaccat cgatactact gaggccccac caatgttttg atcatgtgga caatgttcac    540
ttgattttca actttgaaga aatgacccat ggttgtggaa gcagaggatg gcgccactcc    600
atcacatttc acctaccacc acccgtaaaa tatgcggagc tgtccttgtc ttttttgttg    660
ccaagtaacc tttgccattc tttattgtgc ttttgtatat atactcatcc atagtggctt    720
```

```
ataattcttc aactctccac agaaactcca taggtctctc ttagcctcat tgtttcaaga    780
aaatggtaga tct                                                      793
```

```
<210> SEQ ID NO 6
<211> LENGTH: 984
<212> TYPE: DNA
<213> ORGANISM: Populus sp.
<220> FEATURE:
<221> NAME/KEY: promoter
<222> LOCATION: (1)...(984)
<223> OTHER INFORMATION: cinnamate 4-hydroxylase (C4H) promoter

<400> SEQUENCE: 6
tgatatgaga aactaacgtt gcttgaattc aagatagaaa ttgaccttgc aagaagacaa     60
acgtattctt ggaaacacgt attaataaat acaaagtagt ttgtcacact acggagaaa    120 atatctaata aaagtaagac cttatagttt caggaggtta ggttgatatt taagagaga    180 tttctttat taacttttta tatatgttga aatcttgaaa ttaatattaa aaagatttgt    240 taatccttt ctcttgaata ctttggattg atgtgaggga ttcacattta aactattctt    300
aaatgaatct tgaagctgta tgtttgatat tgtgttttta aaatgtatt atctttaaaa    360 aatatcaaat taatgatttt ttaatgtttt ttaaagatt gaaagtatta atttaaaaaa    420
taaaataaaa ttatttttaat atatttttaa ataaaaaata tttttgaaga gcagactgca   480
ccctatactt gatctcaatt ttaaagagat ttggagaaca caagaattaa aaagaaaag    540 gataggaaaa aaaaactttc ttgtttgata gccttattac ttgaagctga aatcatcata    600
gattagtggc gcccacatta catcttgtat agaaatatag aaaggcctgg caaattaatt    660
aatatgatga ccatatgaca ttttcggcca ccaacccgcc ttacctacta ctatccatga   720
tcatcaatgt cactctccta ccacctcaaa tgtaacgccg ttaactcccc ccccccaca    780 cacacacaca accctagcta gtagccacac gctccaccac ctaacgtgtg aaattcaact   840
tcatttcctc tctaattttt gtagcttata aaacccaagc tctcctcgtc ctgttgctcc   900
catccaacaa ccatcactct tcttacctca aaaatcccca cctctttctg acaaagaaac   960
cagttccaat attatggtag atct                                          984
```

```
<210> SEQ ID NO 7
<211> LENGTH: 1007
<212> TYPE: DNA
<213> ORGANISM: Populus sp.
<220> FEATURE:
<221> NAME/KEY: promoter
<222> LOCATION: (1)...(1007)
<223> OTHER INFORMATION: cinnamoyl CoA reductase (CCR) promoter

<400> SEQUENCE: 7
tgcgctcggg ttgtcaccat agtttcattt cttaatttat taagttaaat taagatacaa     60
taagttggtc acgttttaaa gcaaagagaa acaggaaatg ggtaaaaagc aacataaatt    120
ctctttcaca tttttttgtc accaggttct tgttggtct aggagtatta attaattaat    180
gctttgacat tgatttattc gttaattctt ttaaaacact gaattaaatc caatccacac    240 acaaatgaa atgggggtag gtgatgtggg tgattatttt ttattcggtt tgattttat    300 taaaaaaaat aaccaaactg aattattata ttttttaaaaa aactaaaacc ggttcaaacc    360
ggtcggtttc aattcggttt ttaggacaa caaccggttc aaaccacttt ggctcggttt    420
aggtttgatt cggttcgatt ttttgatttt taggtttata aaacgaaaat tgaactgaac    480
cggttaattt tttaaaaatt taaattttaa tttttttaatt attttctttt taattttttg    540
```

```
attttatcag ttttttcaaat tttttttttca cttaagagag gccatggtca tcatgtacct    600
tcaaagaaga gagagaaata gcaaagcaca tggtgacgtt gtgttgacga ttcacattac    660
aaagacccat actcctactt cacaaacctt aataataata ataataataa taataataat    720
aatagtaata agagaaaaaa ctagaaaaac aaaaacaaag agagaagaat ctctttcctc    780
tctctcagag gcgaatattt accagtagta ggtgaggatg gtaacttcta accttataaa    840
tacatccact ccaccatgtc tttccttgta acatccactt ttcaagccaa gataagaaga    900
aaagacatct cctctcctct ttctctctgt ctgttctcca ctttcccagt caccaaactc    960
gtatacatat aattacattt atctaaatat aacaacatgg tagatct                 1007
```

<210> SEQ ID NO 8
<211> LENGTH: 2081
<212> TYPE: DNA
<213> ORGANISM: Populus sp.
<220> FEATURE:
<221> NAME/KEY: promoter
<222> LOCATION: (1)...(2081)
<223> OTHER INFORMATION: ferulate-5-hydroxylase (F5H) promoter

<400> SEQUENCE: 8

```
ttcagtgaac atgctgccac aatgacatat atatcatcac aaattaatta atgtctactt     60
taatgctgat atatcttttg tttattattt ttttttcctat catgggaaat gagatcaact   120
ttttcagatg aaaattacta attaaactat catatttcca gtttaatcaa agatatggaa   180
tctttatttc actaaagata ttattattca taagaatttg atgagttctt gcattatttg   240
ttagattatc ttcaccctct tgcaattagt gcttcatgga ctccttttt tcttgtgaaa    300 gtagtttgcc atttaaatat agaaatatct catgctttac aaaatataat aatctcccct   360
aagatataat aaattgaact gagatgcaat taagtcggtt aaaaggcctg gatactgcca   420
gtgaataaga tttacacaaa atattggatt ttttcccgtc ctgaaagcta attattgtca   480
gaaaaatacg ttttgaaata gttgattttt attgatatgg tggaataaaa acatcaatgg   540
ttccaatgtc taaccacgaa aatgacttgt aaaatttata ataaggtcta ttttttttcat   600 caagcaataa taataaggtg aggcatcaaa atctctcact ttttgcttct gatcaaagat   660
cactaagcag aacttgcatg gaacctcatc tctctctctc tccccctctc tctctctccc   720 cctctcccctc tctatatata tatatatata tatatatata tatgcaagta ttagtcacat   780
tgcatgagta cgtggcagtt ttggatatgc tttgataacg ataacaccg agagtacaaa    840 acaaaatctg ggtaggtagc tggctcaatt gcaaccaaat aataataaga aattttagct   900
gcaagcaatt aagaaaatga aagattgcac ctatgtcaac cactgggtta atatttatga   960
tcttaatctt ttttttttgt ataatttctt ttatatgccg tgaaatgaag tcagcccctta  1020 agttttacat aaatgtttag gttaattaga aaggagttaa ttctatatat aataagttgt   1080
tgattgaaac aaaatatggt ctgtcactct attttgggt tgcttttat tgcatagtac    1140 ttctgcccta ttgattcagt gaacccttc gtatttataa tataataaag tagaccttga    1200
ataaatattg acatgtaact taaaacatta attgtcctcg ttttgacaac ataaaatctg   1260
tatcaacgta cgtgctcttg tttagggttt tcttagaca actttatatc tagaaaacgt    1320
aattcaatca aaaagatat atatatatat atatatatat atatatatat atatatatat    1380
atatatagac agacgacata acaaaaatgt tcgggtcaga actctggact actgatcgaa   1440
gttgtttcaa atatattgaa tggtatatct taccatagta attaactgag ttatttcaag   1500
```

```
atattacaca gacataacat attttgttct tgatcaaaat atattttatt taaaaatata    1560
ttaaaataat atatttttta ttttaaaaa tatattttta atcaatac attaaaataa       1620 tttaaaatat aaaatacaa aaatattttt taaccacaaa aaaaaaaaac tatgaaaatt     1680
aatgttctta aatattgttc tccatccaga ttttggtacg tatgcgttcc cagtgtgtac    1740
ttgtttatga aagtctactc ttatttttca acttttctca agacattgaa ttagtaaacc    1800
aatgttttac gaattggata cgaaaccttc caaaataata tatatatata tatatatata    1860
tatatatata tatatatata tatatatata tatatatata tatatatata aagagggagg    1920 gaggggtgg gggaggtcac aaaaaacctg tatataaagc cccgtaatat ctttctcagc     1980
ttagcaacat ctgaaagttg caattaatca gtggtgtgta ctgtgatgca cacaatacaa    2040
tacataccat agacacaaac acaaaaatct gcatccatgg a                       2081

<210> SEQ ID NO 9
<211> LENGTH: 995
<212> TYPE: DNA
<213> ORGANISM: Populus sp.
<220> FEATURE:
<221> NAME/KEY: promoter
<222> LOCATION: (1)...(995)
<223> OTHER INFORMATION: sinapyl alcohol dehydrogenase (SAD) promoter

<400> SEQUENCE: 9
taatcgaaac cgatcgattt gaactggttt cttttttttt ttaattttgg tttggttgct    60 ttttttgtc acccctaata attatatata ataatataaa taaaattatt taccattatt     120
tgtctgagat ttttttaat agaatgatta aaatgatatt gtaaaaaaaa cctaataata    180
ccatactttt caaataatat ttttactat tattagtgat tggtttgctg tcaaagttgt    240
tttttttttt tttactattc ttaggagttt gtttcttta ccctagtcta caggagtttg    300
ttagttacta tcatttcttt aaaaaggaaa ctcatatgga aaggaaaaa ttgattaaat    360 acaaaaaatt ataaaattac atagagttttt tatttatttg aacgattgag tttaattta    420 acttaataaa atataattaa ttacaggtaa acaagtact tatcaatcat ataagtata    480 ttataaaaca tattaattat gagttcagca aagatttgtg ctgatttctt gtctcttcta    540
aactacatgt gacaagatag aaaaaacatc taaatgctaa tgattcttta atatatgact   600
atgcaagtca tttatcttat ttaaatacat taatttaaat caaacttaat tttaaattat    660
tggattctaa tataattgtg ttttaaaaca cttaggtagc ttccttgttg gacccgaaac   720
tggttcatga actgaaataa tctatgcgaa taacgtttt ccacaaaaag aagaacgact    780 tgcttttta gcgacaatca tgcctccttc gacctcaccg atgacaccac ctgtgagtgc    840
tgtttgccag taacatcacc tccttgtccc tatgtgtata tagaaagaca aacttgccaa   900
gcataaaaaa gaagaagaag aagtcatact atatatttcc tgccttcctt ctcgacgata   960
tttctctatc tgaagcaagc accatggtag atcta                             995

<210> SEQ ID NO 10
<211> LENGTH: 1269
<212> TYPE: DNA
<213> ORGANISM: Populus sp.
<220> FEATURE:
<221> NAME/KEY: promoter
<222> LOCATION: (1)...(1269)
<223> OTHER INFORMATION: UDP-D-glucuronate carboxy-lyase (UDP) promoter

<400> SEQUENCE: 10
ggaaatgtca acacttgtgt gaccacacgc acactgtaga cgctacctta cctggccaga    60
```

-continued

| | |
|---|---|
| ccccgtcgcc cagggattac aatttaattt gaatttgata atatcatctc aactaacttg | 120 |
| aatgaatatt cttttttttaa cagttgtatt gcttcatgga aaataaatat tgtatatatt | 180 |
| aggatattta atttgaaata aatattatca aatatgactc aaaacccagt ctaatatatt | 240 |
| tatattttga atatgataca atataaacct ttttagtatt aacataatgc atgtgttgaa | 300 |
| taaatatttt tttttattaa ataataaata tggattgaat gtcgaaaaga gaaataaata | 360 |
| gtgtactcat agttacccca tgtacaagtt gagtacaaca acagatgtag tcaaaataaa | 420 |
| agaaaactcg gtctgacgtg tcgttaccat tactgtcatt ggacagtaaa gtctttcgat | 480 |
| tgtaacagaa catgttctcc ttctctctgg ccagtaacga ccgcgaatta cgcttcctcg | 540 |
| aaatttcaat ctaaccttga acactatata agtatatgcc ctgtctctca tcatccgctg | 600 |
| tccttaaatc ccttcaaaat actacaacaa aatatttttt tccctcaatt tatttcagca | 660 |
| gcaaaagtct acgtggtaat taaatctcaa tttccattcg ttttttatagg gattttttggt | 720 |
| tgtctggaga aaaaaataat ggtcatggga ttgagagatt ttgagattca gatctgaagt | 780 |
| ttgtttttaa tttttttcaat aactggtggg gtatggtttt tcgttgattt gaagcattgt | 840 |
| acatttcgtg ttttttgaagt ctcatttaat ttatgcgtcc ctcctttttct ctctcactag | 900 |
| ctggtgttgt ttgttggtgt gtttattatc atgattagtt gttaaccatc tatttttttaa | 960 |
| tctaatttgg ttacaatcga gttctttata taaagctgta gtctttgagt ttcatgactc | 1020 |
| gcagcgaaaa aagtttgaga ttttgactct atttttttcac accactcagg tgaactggat | 1080 |
| ttattatcat gttttttaatt gaacttgtt ggctggtttg atttaaggtt tttgatttgt | 1140 |
| gggttattta tgaatgtgag gattatgcaa tgttttgttt ctgggttgtt tttacaattt | 1200 |
| atggtggatt gattttttttt tttaatttttc atgattttca gaaattggac aagaatgtca | 1260 |
| gatctgata | 1269 |

<210> SEQ ID NO 11
<211> LENGTH: 1025
<212> TYPE: DNA
<213> ORGANISM: Populus sp.
<220> FEATURE:
<221> NAME/KEY: promoter
<222> LOCATION: (1)...(1025)
<223> OTHER INFORMATION: lipid transfer protein (LTP) promoter

<400> SEQUENCE: 11

| | |
|---|---|
| gaattcgatt acgatgaaat gaagaactga tagcataatc aatcagaaga ttgataatta | 60 |
| ttcaaaataa ttttttcgaac aatattcaat gcatgatgat tatatgtcgg atcaataaat | 120 |
| aatcaattta atgtaaaaaa gggggtactta agtaaataat aataataata ataatgaatg | 180 |
| ccttagcatc taaaattcgc tatttttaga agaatcacat tccaagcttc atgaacaatc | 240 |
| taatgttcaa tgacatttga tatttttaat aattcaagaa tctcaacaat acaagaatca | 300 |
| ttggcatcgc aagatatttt ccctaagcaa gctctaaaat ccccgtacaa acatcctttt | 360 |
| aaggtatata tattagttcg aaaataatta tgtgttaatc ttcatgtgca gtggtgagta | 420 |
| tttcggccat tcaggcgggt gacccgggat cgttccccag caacggcgtc agttttaatt | 480 |
| tttatgttttt cttgaaagtt ttcttaattc ttggcgctgg cttttttgggt ggaaggaacg | 540 |
| cggtgttgcg aaaggtaatg gccactaatt gggcaagata atggcatgtc tgtgttgcgg | 600 |
| tagttggctc aaaggggagc tttgtggtgg tggtaatatt ggagttctag tcttctagag | 660 |
| acccactgag atggctggat aatgagcttc aagggttaat tttgcgctgt cattaaaatg | 720 |

| | |
|---|---:|
| gtaacatctg gatatatgca atggaatggg atgatatggc acccaaatca ccaacctttg | 780 |
| attggactgg aaagaactat aatttacaac actaattttc taaagccaag tgctgcaata | 840 |
| atatcaactt gtctcttgtt gtagtgctag ccccatttg attagtggac tgggcatcga | 900 |
| gttgaggttc atcttgcagt ataaaagctg tccataggag taggagcatt gcattcccat | 960 |
| acagcaagaa aatcaatttg ttcatatata tagttgagat acagaaatat ggaggctcca | 1020 |
| gatct | 1025 |

```
<210> SEQ ID NO 12
<211> LENGTH: 2341
<212> TYPE: DNA
<213> ORGANISM: Populus sp.
<220> FEATURE:
<221> NAME/KEY: promoter
<222> LOCATION: (1)...(2341)
<223> OTHER INFORMATION: ag-13 (AG13) promoter

<400> SEQUENCE: 12
```

| | |
|---|---:|
| gaattcgcat ccatgcggtg agttcgcatt ggtttgatcc aagtggaaca tttccatacc | 60 |
| cacaccccca ttagcataac aatcctttat taaaccacta gctagacatg caagattcaa | 120 |
| cctacacaca agaaccccact agatagactt ccactggaaa catgcagcat tctcccgtga | 180 |
| tgacctcatt actcagtctt ttctactggg gtttctgttt caaccttctc ctctgtttca | 240 |
| acaggcttct gttcttcctt ttcttcttct tcctttgggg cttcgactgc aacctccgct | 300 |
| tcttctgccg gtgcctcacc aggccctgta gtctctttag cctcctcgac aacaggctct | 360 |
| acgggtatat ccggctcctc ttttgtctcc tcaacaaccg gctctggtgt ttccttaggt | 420 |
| gtctcctcct cagttttctc tagtaccgtt ggctcttctg cagcgatctt ggtctcttcg | 480 |
| agcacttctt tagtttcagc ttcagctggg gcctcgggct ctggtgccac gggctcctca | 540 |
| gatgctgcaa ctttctctgc ttcttttggc tcttcatgag ttactgcctc tggtgctgca | 600 |
| gtgaccgctt cttctgtggt ggtctcaacc ttgattggtt gttcatttt ttcctctaca | 660 |
| agtgcattct gcgctgacac aacctgcagg atacgttatt aaaagaaaag aatgttcacc | 720 |
| aaaatgctga tgaggtctta ccatttgtta tatatataga gatgaatata cgaattttca | 780 |
| aatatgaaca tccacgaatt aaagatcata attaagatgg aggtgttgat cttgatgtac | 840 |
| attccatcag cataaaactt atcagagtta tatataaaa tatatttaat gacttggaag | 900 |
| aagtaataga tgaaatctgt taaataaact tctcaagagg gagattaaat cattcttagt | 960 |
| gaatgagtta cctcaacagt ggccattgga actagaagga aaataaagca cagctgggat | 1020 |
| gcaaaagaaa actgtaagaa gcaaaaaggt acgttggagt aattatcaca gaagaggatg | 1080 |
| aagaaattgc tttgagtatt tgatgcagag tactgatgaa cgagggtgga tttatataga | 1140 |
| gatgtagggg gctcactcga gcgagggagg gagtgagtga gagaagagag ctaccgtccg | 1200 |
| aggaatcttg ggatctgaca ccatagctga tgtcattaaa gaattgttgg aagtgaattc | 1260 |
| cttttttagaa tattttttat ttataaatat attataataa tattttttat tttttaaaat | 1320 |
| ttattttgat atatgtatat taaaaagaat aaaaataaaa attaaatttt aacaaatctc | 1380 |
| catttgggca cacgatttaa tttgaaaagg ctaaaataat ggaggccatt ttcatcttag | 1440 |
| ccatcatctt cttttggtcg cgtgtgctga tgtgctttgt gcagtcggtc atgtaggtga | 1500 |
| ttatcatcca ttcatgttct caacttgcca ttcgtcatta acaactcctc ccttttttt | 1560 |
| cttttttttt taaggataaa tgaattaatt ttttaagaaa ataatgaaaa taatttgtca | 1620 |
| aaaatttag aaataaaaaa ttccaacaat gctgggtcac taaaattatt aataatattt | 1680 |

-continued

```
aagaaataaa agcaattgac caaaagaact tcaaaaaaa gctatcttta tttttttttt    1740
taatatttct caatatttgc ttgcactata aactagtact gtgatttcct catgttaaat    1800
aataataata ataataataa tcacccttaa ccaataggca taatttactt caaacaagcg    1860
aataaaactc tgacgtggaa atttaagttg gtcccacgct ctctctcggc cattgcttta    1920
tcaattatgg tatttcataa aaaatttaat ttttttttaaa tagttttaat atattaatat   1980
taaaaataat ttttaaaata aaaaatatta ttttaatata tctttaaatt aaaactactt    2040
taataaacaa gctatcacat tatcaaacgc tatttaaagt cggcggatcc cacgagatgc    2100
agggatagca acattagtgt aggactggat cagctgagct ggagctggtg gacggccatg    2160
tccacggatt tcgtcgctgt cgattacgtg tcaacagttt ttttttatat tattttcttc    2220
tacttttcca gatggatcca agcctccaag aacgaaacat tggctacagt ttgaaaactc    2280
ttaaaaatgt taagattaat aagattagca gcatcatatt aagtcaagga atgtcagatc    2340
t                                                                    2341
```

<210> SEQ ID NO 13
<211> LENGTH: 31
<212> TYPE: DNA
<213> ORGANISM: Artificial Sequence
<220> FEATURE:
<223> OTHER INFORMATION: primer/oligonucleotide

<400> SEQUENCE: 13
gccatagctc cttaagagaa acagaaagca a                              31

<210> SEQ ID NO 14
<211> LENGTH: 32
<212> TYPE: DNA
<213> ORGANISM: Artificial Sequence
<220> FEATURE:
<223> OTHER INFORMATION: primer/oligonucleotide

<400> SEQUENCE: 14
caatatagaa tcaatgaaca gcactagttt gc                             32

<210> SEQ ID NO 15
<211> LENGTH: 20
<212> TYPE: DNA
<213> ORGANISM: Artificial Sequence
<220> FEATURE:
<223> OTHER INFORMATION: primer/oligonucleotide

<400> SEQUENCE: 15
tcatgtccta tccaacggcg                                           20

<210> SEQ ID NO 16
<211> LENGTH: 24
<212> TYPE: DNA
<213> ORGANISM: Artificial Sequence
<220> FEATURE:
<223> OTHER INFORMATION: primer/oligonucleotide

<400> SEQUENCE: 16
ctcattttct ctcaaagctc aaag                                      24

<210> SEQ ID NO 17
<211> LENGTH: 30
<212> TYPE: DNA
<213> ORGANISM: Artificial Sequence
<220> FEATURE:

<223> OTHER INFORMATION: primer/oligonucleotide

<400> SEQUENCE: 17
gacaactagt ctaaagttaa aacttagacc                              30

<210> SEQ ID NO 18
<211> LENGTH: 20
<212> TYPE: DNA
<213> ORGANISM: Artificial Sequence
<220> FEATURE:
<223> OTHER INFORMATION: primer/oligonucleotide

<400> SEQUENCE: 18
ccctggaggt tggggtgagt                                          20

<210> SEQ ID NO 19
<211> LENGTH: 25
<212> TYPE: DNA
<213> ORGANISM: Artificial Sequence
<220> FEATURE:
<223> OTHER INFORMATION: primer/oligonucleotide

<400> SEQUENCE: 19
gcgttcatct acaaaaccct cctcc                                    25

<210> SEQ ID NO 20
<211> LENGTH: 23
<212> TYPE: DNA
<213> ORGANISM: Artificial Sequence
<220> FEATURE:
<223> OTHER INFORMATION: primer/oligonucleotide

<400> SEQUENCE: 20
ttcatcctta tttttttggg ata                                      23

<210> SEQ ID NO 21
<211> LENGTH: 20
<212> TYPE: DNA
<213> ORGANISM: Artificial Sequence
<220> FEATURE:
<223> OTHER INFORMATION: primer/oligonucleotide

<400> SEQUENCE: 21
caaaggatca tggagttgga                                          20

<210> SEQ ID NO 22
<211> LENGTH: 34
<212> TYPE: DNA
<213> ORGANISM: Artificial Sequence
<220> FEATURE:
<223> OTHER INFORMATION: primer/oligonucleotide

<400> SEQUENCE: 22
tatactaata tgacctaata acttagaagt gtgg                          34

<210> SEQ ID NO 23
<211> LENGTH: 22
<212> TYPE: DNA
<213> ORGANISM: Artificial Sequence
<220> FEATURE:
<223> OTHER INFORMATION: primer/oligonucleotide

<400> SEQUENCE: 23
catcttgatc aagattgaat tc                                       22

```
<210> SEQ ID NO 24
<211> LENGTH: 20
<212> TYPE: DNA
<213> ORGANISM: Artificial Sequence
<220> FEATURE:
<223> OTHER INFORMATION: primer/oligonucleotide

<400> SEQUENCE: 24
cataatatca aaacttaagc                                              20

<210> SEQ ID NO 25
<211> LENGTH: 33
<212> TYPE: DNA
<213> ORGANISM: Artificial Sequence
<220> FEATURE:
<223> OTHER INFORMATION: primer/oligonucleotide

<400> SEQUENCE: 25
tgaattgatg acgtaggaaa catgataaac atg                               33

<210> SEQ ID NO 26
<211> LENGTH: 28
<212> TYPE: DNA
<213> ORGANISM: Artificial Sequence
<220> FEATURE:
<223> OTHER INFORMATION: primer/oligonucleotide

<400> SEQUENCE: 26
cattttcttg aaacaatgag gctaagag                                     28

<210> SEQ ID NO 27
<211> LENGTH: 29
<212> TYPE: DNA
<213> ORGANISM: Artificial Sequence
<220> FEATURE:
<223> OTHER INFORMATION: primer/oligonucleotide

<400> SEQUENCE: 27
gacatgagaa actaacgttg cttgaattc                                    29

<210> SEQ ID NO 28
<211> LENGTH: 33
<212> TYPE: DNA
<213> ORGANISM: Artificial Sequence
<220> FEATURE:
<223> OTHER INFORMATION: primer/oligonucleotide

<400> SEQUENCE: 28
cataatattg gaactggttt ctttgtcaga aag                               33

<210> SEQ ID NO 29
<211> LENGTH: 25
<212> TYPE: DNA
<213> ORGANISM: Artificial Sequence
<220> FEATURE:
<223> OTHER INFORMATION: primer/oligonucleotide

<400> SEQUENCE: 29
gcgctcgggt tgtcaccata gtttc                                        25

<210> SEQ ID NO 30
<211> LENGTH: 26
<212> TYPE: DNA
<213> ORGANISM: Artificial Sequence
<220> FEATURE:
<223> OTHER INFORMATION: primer/oligonucleotide
```

```
<400> SEQUENCE: 30
catgttgtta tatttagata aatgta                                      26

<210> SEQ ID NO 31
<211> LENGTH: 29
<212> TYPE: DNA
<213> ORGANISM: Artificial Sequence
<220> FEATURE:
<223> OTHER INFORMATION: primer/oligonucleotide

<400> SEQUENCE: 31
ttcatcaagc aataataata aggtgaggc                                   29

<210> SEQ ID NO 32
<211> LENGTH: 26
<212> TYPE: DNA
<213> ORGANISM: Artificial Sequence
<220> FEATURE:
<223> OTHER INFORMATION: primer/oligonucleotide

<400> SEQUENCE: 32
catggatgca gattttttgtg tttgtg                                     26

<210> SEQ ID NO 33
<211> LENGTH: 26
<212> TYPE: DNA
<213> ORGANISM: Artificial Sequence
<220> FEATURE:
<223> OTHER INFORMATION: primer/oligonucleotide

<400> SEQUENCE: 33
ttcagtgaac atgctgccac aatgac                                      26

<210> SEQ ID NO 34
<211> LENGTH: 26
<212> TYPE: DNA
<213> ORGANISM: Artificial Sequence
<220> FEATURE:
<223> OTHER INFORMATION: primer/oligonucleotide

<400> SEQUENCE: 34
aatcgaaacc gatcgatttg aactgg                                      26

<210> SEQ ID NO 35
<211> LENGTH: 21
<212> TYPE: DNA
<213> ORGANISM: Artificial Sequence
<220> FEATURE:
<223> OTHER INFORMATION: primer/oligonucleotide

<400> SEQUENCE: 35
catggtgctt gcttcagata g                                           21

<210> SEQ ID NO 36
<211> LENGTH: 28
<212> TYPE: DNA
<213> ORGANISM: Artificial Sequence
<220> FEATURE:
<223> OTHER INFORMATION: primer/oligonucleotide

<400> SEQUENCE: 36
ggaaatgtca acacttgtgt gaccacac                                    28

<210> SEQ ID NO 37
<211> LENGTH: 23
```

```
<212> TYPE: DNA
<213> ORGANISM: Artificial Sequence
<220> FEATURE:
<223> OTHER INFORMATION: primer/oligonucleotide

<400> SEQUENCE: 37
gacattcttg tccaatttct gaa                                         23

<210> SEQ ID NO 38
<211> LENGTH: 24
<212> TYPE: DNA
<213> ORGANISM: Artificial Sequence
<220> FEATURE:
<223> OTHER INFORMATION: primer/oligonucleotide

<400> SEQUENCE: 38
ggagcctcca tatttctgta tctc                                        24

<210> SEQ ID NO 39
<211> LENGTH: 28
<212> TYPE: DNA
<213> ORGANISM: Artificial Sequence
<220> FEATURE:
<223> OTHER INFORMATION: primer/oligonucleotide

<400> SEQUENCE: 39
caagacgatg aaatgaagaa ctgatagc                                    28

<210> SEQ ID NO 40
<211> LENGTH: 26
<212> TYPE: DNA
<213> ORGANISM: Artificial Sequence
<220> FEATURE:
<223> OTHER INFORMATION: primer/oligonucleotide

<400> SEQUENCE: 40
gacattcctt gacttaatat gatgct                                      26

<210> SEQ ID NO 41
<211> LENGTH: 26
<212> TYPE: DNA
<213> ORGANISM: Artificial Sequence
<220> FEATURE:
<223> OTHER INFORMATION: primer/oligonucleotide

<400> SEQUENCE: 41
gaattcgcat ccatgcggtg agttcg                                      26
```

CAMBIUM/XYLEM-PREFERRED PROMOTERS AND USES THEREOF

RELATED APPLICATION

This application is a §371 of PCT/BR2005/00041 filed Mar. 28, 2005 which claims priority of application Ser. No. 60/560,227 filed Apr. 6, 2004, and incorporated by reference in its entirety.

FIELD OF THE INVENTION

The invention relates generally to the field of molecular biology, biochemistry and agriculture. More particularly, the invention relates to polynucleotides suitable for regulating gene expression in plants and generation of transgenic plants with improved quality and productivity.

BACKGROUND AND PRIOR ART OF THE INVENTION

Modification of a plant trait through genetic engineering depends upon the insertion into the plant genome of a polynucleotide construct containing the gene of interest, operably linked to a promoter that is functional in the transgenic plant. Within a plant genome, any single gene is, in general, operably linked to a promoter that will determine when and where, within the plant tissues and organs, the gene should be expressed. Therefore if one wants to express a gene of interest in specific tissues or organs within a transgenic plant and in a temporally regulated manner, tissue-preferred promoters must be used. On the other hand, expression in all plant tissues throughout the plant's life cycle could by achieved by using constitutive promoters.

In a number of situations the expression of particular genes in particular tissues or organs confers a specific phenotype of interest to the plant. For example, if one wants to improve the nutritional quality of cereal seeds, a gene that confers such phenotype using seed-specific promoters is inserted, rather than using constitutive promoters that would allow the gene to be expressed in all plant tissues causing, in some cases, undesirable phenotypes. In another example, if one wants to increase the amount of cellulose in the developing vascular tissues of a forest tree, one would introduce into the plant genome a xylem- and/or cambium-preferred promoter operably linked to a heterologous gene encoding an enzyme involved in cellulose metabolism such that more cellulose molecules could be produced in the developing plant xylem. In another example, the desired phenotype could be obtained by inhibiting the expression of an endogenous gene within a specific plant tissue. This could be done by introducing a construct comprising a tissue-preferred promoter operably linked to a polynucleotide that would inhibit the expression of the endogenous gene, either by anti-sense hybridization or by RNA silencing (Matzke (ed.) et al. (2000) *Plant Gene Silencing* Kluwer Academic Publishers).

Thus far, the production of genetically engineering plants expressing useful and/or desirable traits requires the availability of promoters that permit the gene or genes of interest to be expressed in a tissue- and timing-specific manner. Thus, isolation and characterization of tissue-preferred, particularly cambium/xylem-preferred, promoters that can serve as regulatory regions for expression of heterologous nucleotide sequences of interest in a tissue-preferred manner is essential for the genetic engineering of plants exhibiting particular traits.

SUMMARY OF THE INVENTION

The present invention relates to isolated regulatory nucleic acid molecules from the genome of *Populus* sp, and methods for regulating expression of heterologous nucleotide sequences in plant tissues, such as in a xylem and/or cambium-preferred manner. It is an object of the invention to provide isolated nucleic acid molecules which represent promoters able to direct tissue-specific expression of genes of interest. The regulatory nucleic acid molecules of the present invention correspond to promoter sequences of genes which are preferably expressed in the cambium and/or in the xylem of *Populus* sp. Genes encoding isoforms of sucrose synthase (SuSy), alpha-tubulin (TUB), arabinogalactan protein (ARAB), caffeic acid 3-O-methyltransferase (COMT), cinnamyl alcohol dehydrogenase (CAD), cinnamate 4-hydroxylase (C4H), cinnamoyl CoA reductase (CCR), ferulate-5-hydroxylase (F5H), sinapyl alcohol dehydrogenase (SAD), UDP-D-glucuronate carboxy-lyase (UDP), lipid transfer protein (LTP) and ag-13 (AG13) were found to be expressed in the cambium/xylem tissue of *Populus* sp. and their promoters, which are the subject of the invention, have been isolated, cloned and validated. When these promoters are associated in a transgenic plant with genes other than those to which they were originally linked, the genes in question are preferably expressed in the cambium and/or in the xylem of said transgenic plant. Methods of using the cambium/xylem-preferred promoters disclosed herein, for regulating expression of heterologous nucleotide sequences in cambium and/or xylem-preferred manner in a plant, are provided.

The cambium/xylem-preferred promoters were identified through the analysis of a collection of Expressed Sequence Tags (ESTs) from *Populus* sp, representing apical shoot, bark, cambium, seed, xylem, leaf and root tissue. Based on the expression profile of those ESTs among the different tissues, the twelve genes referred to supra were shown to be highly and preferably expressed in the cambium and/or in the xylem of *Populus*.

The cambium/xylem-preferred promoters of the invention are set forth at SEQ ID NOS.: 1-12. Fragments of these nucleotide sequences, i.e., those set forth in SEQ ID NOS.: 1-12 comprising at least 20 consecutive nucleotides are also a feature of this invention. The smaller fragments, while not necessarily encoding promoters or proteins with promoter activity, can function as antisense molecules and disable naturally occurring and expressed genes. The compositions of the invention further comprise nucleotide sequences having at least 65% identity to the sequences set forth in SEQ ID NOS.: 1-12 or a fragment thereof, and nucleotide sequences that hybridize under high stringency conditions to any one of the aforementioned sequences.

"Stringent conditions" as used herein, refers to parameters with which the art is familiar, such as hybridization in 3.5× SSC, 1×Denhardt's solution, 25 mM sodium phosphate buffer (pH 7.0), 0.5% SDS, and 2 mM EDTA for 18 hours at 65° C., followed by 4 washes of the filter at 65° C. for 20 minutes, in 2×SSC, 0.1% SDS, and a final wash for up to 20 minutes in 0.5×SSC, 0.1% SDS, or 0.3×SSC and 0.1% SDS for greater stringency, and 0.1×SSC, 0.1% SDS for even greater stringency. Other conditions may be substituted, as long as the degree of stringency is equal to that provided herein, using a 0.5×SSC final wash.

Other facets of the present invention include constructs, such as expression vectors comprising the promoters operably linked to a nucleotide sequence of interest, which encodes a desired protein. The promoters disclosed herein are capable of driving expression of polynucleotides of interest in a plant cell and said promoters comprise any one of the nucleotide sequences of the present invention.

Also a part of the invention are recombinant plants or plant cells having stably incorporated into their genomes any one of the constructs described above or the promoter itself.

Methods of the invention also include methods for stably incorporating the products of the invention into cells.

DETAILED DESCRIPTION OF THE PREFERRED EMBODIMENTS

Figure 1:
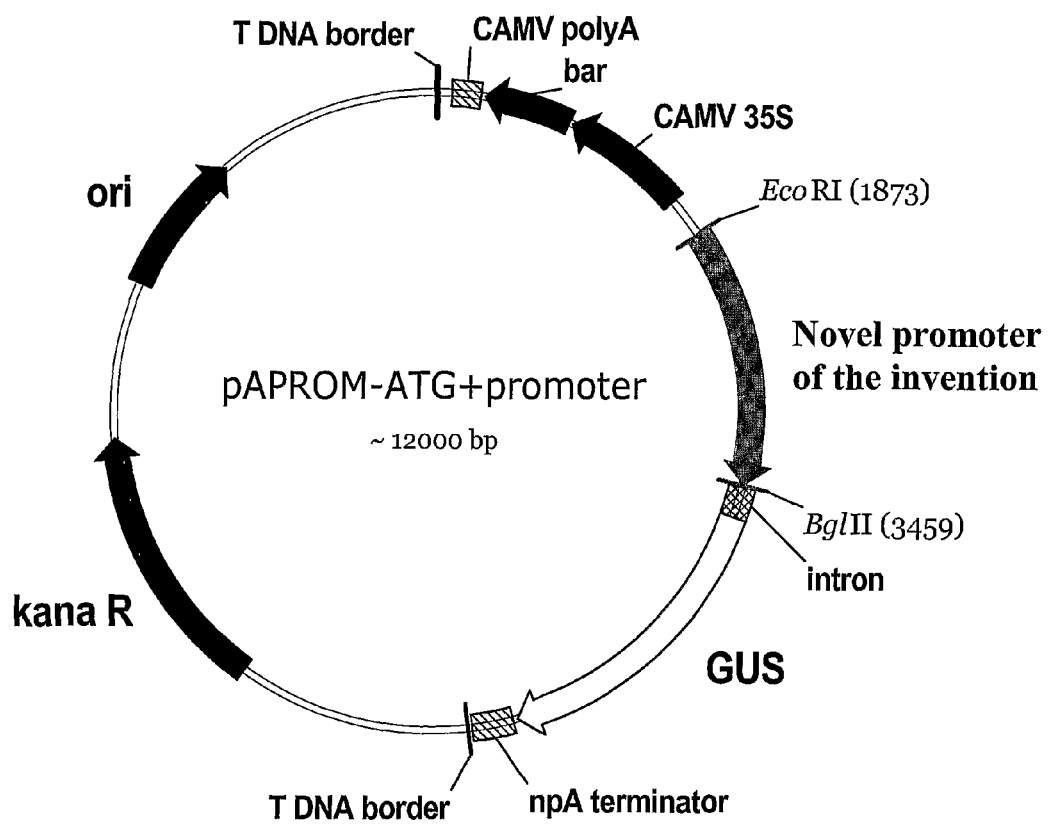
FIG. 1 schematically illustrates the plasmid vector pAPROM-ATG+ promoter comprising the GUS reporter gene operably linked to a promoter sequence. Promoters of the invention were cloned in this plasmid vector in substitution of the represented promoter sequence.

The compositions of the present invention comprise novel nucleotide sequences for plant promoters, particularly cambium/xylem-preferred promoters for the *Populus* (woody aspen) genes encoding sucrose synthase (SuSy), alpha-tubulin (TUB), arabinogalactan protein (ARAB), caffeic acid 3-O-methyltransferase (COMT), cinnamyl alcohol dehydrogenase (CAD), cinnamate 4-hydroxylase (C4H), cinnamoyl CoA reductase (CCR), ferulate-5-hydroxylase (F5H), sinapyl alcohol dehydrogenase (SAD), UDP-D-glucuronate carboxy-lyase (UDP), lipid transfer protein (LTP) and ag-13 (AG13). The nucleotide sequences for these promoters are set forth in SEQ ID NOS.: 1-12, respectively. These promoters were isolated from the 5' untranslated region flanking the transcription initiation sites of their respective genes. Methods for the isolation of the promoters are well known in the art and include bioinformatic tools for gene assembly such as Phred, Phrap, Consed (Gordon et al. (1998) *Genome Research.* 8:195-202), sequence alignment (Durbin et al. (1998) *Biological sequence analysis—probabilistic models of proteins and nucleic acids*. Cambridge University Press, Cambridge, UK), functional search (Altschul et al. (1997) *Nucleic Acid Res:* 25:3389-3402) and PCR techniques (Sambrook and Russell (2001) *Molecular Cloning—a laboratory manual*. Cold Spring Harbor Laboratory Press, Cold Spring Harbor, N.Y., USA). Some of these methods are described in Example 1 supra, and all are incorporated by reference.

In various embodiments, the isolated nucleic acid molecules span 0.1 kb, 0.5 kb, 1 kb, 2 kb, 3 kb, 4 kb or 5 kb starting at the ATG start codon for the coding region of the genes in question. The isolated nucleic acid molecules are referred to herein as promoters. Promoters correspond to the nucleic acid molecules whose function is to regulate the expression of a gene. A promoter generally comprises specific signaling sequences called boxes, arranged along the promoter sequence, such that its composition determines the temporal and spatial expression of a gene that is under its regulatory control. "Promoter" or "transcriptional initiation region" means a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that, having identified the nucleotide sequences for the promoter regions disclosed herein, it is within the state of the art to isolate and identify further regulatory elements in the 5' untranslated region upstream from the particular promoter regions identified herein.

Thus the promoter regions disclosed herein are generally further defined by additional upstream regulatory elements such as those responsible for tissue and temporal expression of the coding sequence, enhancers and the like. In the same manner, the promoter elements, which enable expression in the desired tissue such as xylem and/or cambium, can be identified, isolated and used with other core promoters to confer cambium/xylem-preferred expression.

In the present invention, promoters that regulate the expression of genes specifically in the cambium and/or xylem were identified and isolated from *Populus* sp.

Figure 2:
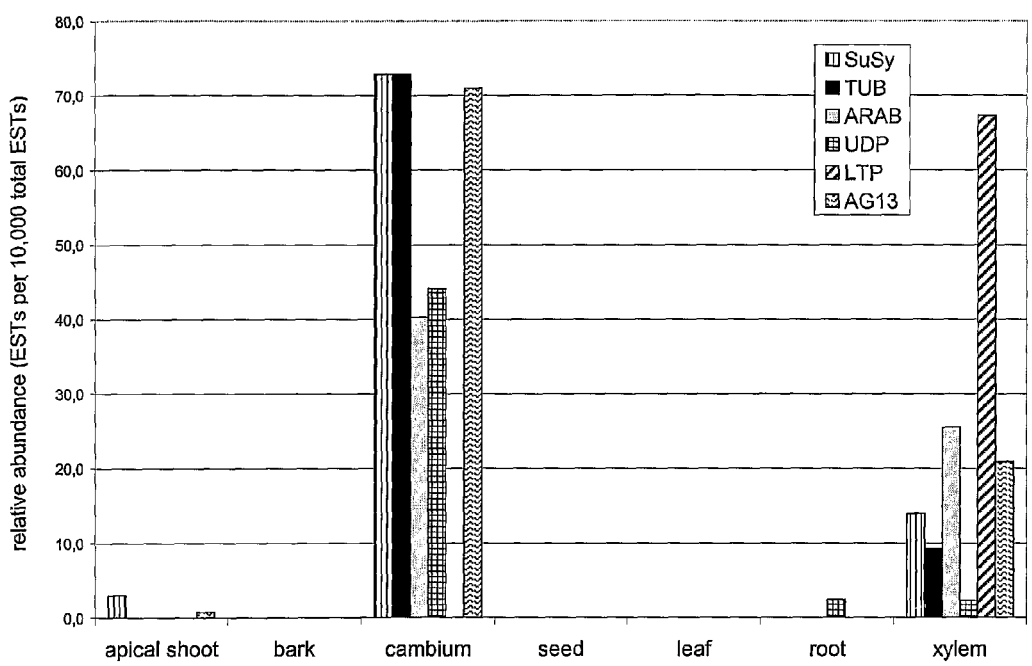
FIG. 2 shows the expression profile in a set of *Populus* tissues of SuSy, TUB, ARAB, UDP, LTP and AG13 genes, which are under the control of the promoters of the invention in *Populus*.

The SuSy gene encodes an isoform of sucrose synthase, an enzyme involved in the conversion of sucrose into UDP-glucose in the developing xylem. UDP-glucose is the building block of cellulose that is synthesized and deposited in the plant cell wall. The SuSy gene disclosed herein is preferentially expressed in the cambium/xylem of *Populus* sp, although low levels of expression can be observed in other tissues (FIG. 2).

The TUB gene encodes an isoform of alpha-tubulin, a structural globular protein involved in the formation of microtubules, which are part of the cytoskeleton. The TUB gene disclosed herein is preferentially expressed in the cambium and/or xylem of *Populus* sp, although low levels of expression can be observed in other tissues (FIG. 2).

The ARAB gene encodes an isoform of arabinogalactan protein, member of a large family of plant cell wall-associated glycoproteins of unknown function. The ARAB gene disclosed herein is preferentially expressed in the cambium/xylem of *Populus* sp, although low levels of expression can be observed in other tissues (FIG. 2).

Figure 3:
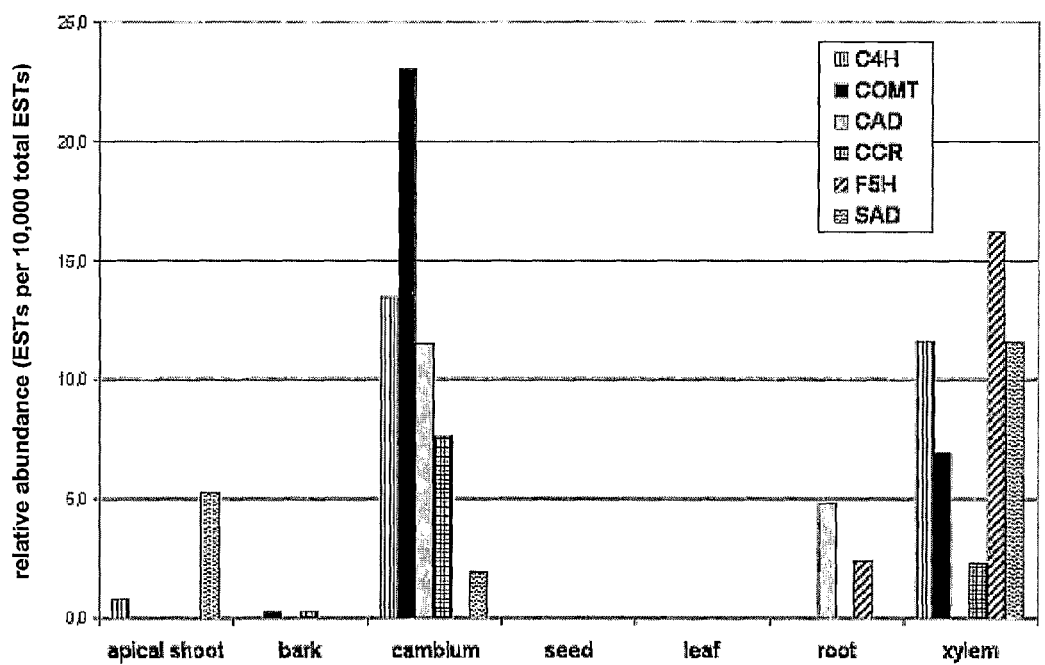
FIG. 3 shows the expression profile in a set of *Populus* tissues of COMT; CAD, C4H, CCR, F5H and SAD genes, which are under the control of the promoters of the invention in *Populus*.

The COMT gene encodes an isoform of caffeic acid 3-O-methyltransferase implicated in the methylation of both caffeic acid and 5-hydroxyferulic acid. These are intermediate compounds of lignin biosynthesis. The COMT gene disclosed herein is preferentially expressed in the cambium/xylem of *Populus* sp, although low levels of expression can be observed in other tissues (FIG. 3).

The CAD gene encodes an isoform of cinnamyl alcohol dehydrogenase, an enzyme that catalyzes the final step in the synthesis of monolignols, thereby converting the cinnamaldehydes to their corresponding alcohols. The CAD gene disclosed herein is preferentially expressed in the cambium/xylem of *Populus* sp, although low levels of expression can be observed in other tissues (FIG. 3).

The C4H gene encodes an isoform of cinnamate 4-hydroxylase, a member of the cytochrome P450 monooxygenase superfamily involved in the catalysis of the first oxidative reaction in the phenylpropanoid metabolism, namely the conversion of trans-cinnamic acid to p-coumaric acid. The C4H gene disclosed herein is preferentially expressed in the cambium/xylem of *Populus* sp, although low levels of expression can be observed in other tissues (FIG. 3).

The CCR gene encodes an isoform of cinnamoyl CoA reductase, which catalyzes the conversion of cinnamoyl CoA esters to their corresponding cinnamaldehydes, i.e., the first specific step in the synthesis of lignin monomers. The CCR gene disclosed herein is preferentially expressed in the cambium/xylem of *Populus* sp, although low levels of expression can be observed in other tissues (FIG. 3).

The F5H gene encodes a cytochrome P450-dependent monooxygenase that catalyzes the hydroxylation of ferulic acid in a biosynthesis directed towards sinapic acid and syringyl lignin. The F5H gene disclosed herein is preferentially expressed in the cambium/xylem of *Populus* sp, although low levels of expression can be observed in other tissues (FIG. 3).

The SAD gene encodes a sinapyl alcohol dehydrogenase that mediates the reduction of sinapaldehyde into syringyl monolignols in angiosperms. The SAD gene disclosed herein is preferentially expressed in the cambium/xylem of *Populus* sp, although low levels of expression can be observed in other tissues (FIG. 3).

The UDP gene encodes the enzyme UDP-D-glucuronate carboxy-lyase involved in the breakdown of UDP-D-glucuronate into UDP-D-xylose and $CO_2$. The UDP gene disclosed herein is preferentially expressed in the cambium/xylem of *Populus* sp, although low levels of expression can be observed in other tissues (FIG. 3).

The LTP gene encodes an isoform of lipid transfer protein, a member of a family thought to participate in cutin formation, embryogenesis, defense reactions against phytopathogens, symbiosis, and the adaptation of plants to various environmental conditions. The LTP gene disclosed herein is preferentially expressed in the cambium/xylem of *Populus* sp, although low levels of expression can be observed in other tissues (FIG. 3).

The AG13 gene encodes an ag-13 protein of unknown function, whose expression has been associated with the ripening process in several plant species. The AG13 gene disclosed herein is preferentially expressed in the cambium/xylem of *Populus* sp, although low levels of expression can be observed in other tissues (FIG. 3).

The cambium/xylem-preferred promoter sequences of the present invention drive the expression of operably linked nucleotide sequences in a cambium/xylem-preferred manner. EXAMPLE 4 illustrates the expression of the GUS reporter gene in the cambium/xylem vessels/fiber complex of *Arabidopsis thalialia* transformed with a construct containing the GUS reporter gene operably linked to two cambium/xylem-preferred promoters of the invention, i.e., the TUB (SEQ ID.: 2) and C4H (SEQ ID.: 6) promoters. EXAMPLE 4 also summarizes results showing expression of the GUS reporter gene in *Arabidopsis* plants transformed with constructs containing the GUS reporter gene operably linked to each one of the promoter sequences disclosed herein. Thus, the cambium/xylem-preferred promoter sequences disclosed herein can be used to express an operably linked sequence of interest in the cambium and/or in the xylem. Hence, the cambium/xylem-preferred promoters can be used to improve the wood quality of trees either by increasing the synthesis of cellulose or by decreasing the synthesis of lignin. "Decreasing lignin synthesis" means decreasing the total lignin content of woody trees by anywhere from 1-90%, preferably by about 80-90% relative to the lignin content in normal field grown plants. "Increasing cellulose synthesis" means increasing the total cellulose content of woody trees by 1-90%, preferably by about 80-90%, compared with normal field grown plants.

In addition, the cambium/xylem-preferred promoters can be used to inhibit the expression of genes involved in the metabolism of developing xylem. The inhibition of such genes decreases the concentration of lignin and/or changes the relationship between guaiacyl and syringyl, the building blocks of lignins. The monomeric composition of lignins is an important characteristic from the industrial point of view, because syringyl unit-rich lignins are more easily degraded during the pulping process, as they contain fewer strong 5-5' carbon bonds. Thus, the determination of the syringyl to guaiacyl (S/G) ratio is useful in evaluating wood quality for cellulose production and papermaking (Boudet et al., 1998). "Changing the relationship between syringyl and guaiacyl" refers to increasing the syringyl/guaiacyl ratio by 1-90%, preferably from about 80-90% compared with normal field grown plants.

Other nucleic acid molecules within the invention are variants and/or fragments of the cambium/xylem-preferred promoter sequences such as those that encode fragments, analogs or derivatives of native cambium/xylem-preferred promoter sequences disclosed herein. Such variants and/or fragments may be, e.g., naturally occurring variants of native cambium/xylem-preferred promoter sequences, or non-naturally occurring variants of cambium/xylem-preferred promoter sequences. For example, the nucleotide sequence of such variants and/or fragments can include, deletions, additions, and/or substitutions of one or more nucleotides as compared to the native cambium/xylem-preferred promoter sequences. Such variants and/or fragments may retain the biological activity and therefore drive, in a cambium/xylem-preferred manner, the expression of operably linked nucleotide sequences. Fragments of cambium/xylem-preferred promoter sequences comprise from about 10, to about 4000 nucleotides or up to the number of nucleotides in the full-length cambium/xylem-preferred promoter sequences disclosed herein as, such as the 700-3500 nucleotides of SEQ ID NOS.: 1-12.

"Variants" is intended to include substantially similar sequences. Naturally and non-naturally occurring "variants" of cambium/xylem-preferred promoter sequences within the invention are nucleic acid molecules having at least 65% sequence identity with the native cambium/xylem-preferred promoter sequences disclosed herein, i.e., SEQ ID NOS: 1-12. "Variants" also include nucleic acids molecules that hybridize under stringent conditions, as defined herein, to the cambium/xylem-preferred promoter nucleic acid sequences of SEQ ID NOS.: 1-12 or the complement of the sequences of SEQ ID NOS.: 1-12. For example, such "variants" may be nucleic acid molecules that hybridize to the sequence of SEQ ID NOS.: 1-12 or the complement of the sequences of SEQ ID NOS: 1-12 under low stringency conditions, moderate stringency conditions, or high stringency conditions. Alternatively, such nucleic acids are those having a nucleotide sequence that is the complement of the full-length or portions of the sequences of SEQ ID NOS.: 1-12. Other variants of cambium/xylem-preferred promoter sequences within the invention are polynucleotides that share at least 65% sequence identity, preferably at least 80%, more preferably at least 90%, and most preferably at least 95%, to the sequences of SEQ ID NOS: 1-12 or the complement of the sequences of SEQ ID NOS: 1-12.

"Stringent conditions", as used herein, refers to the parameters set forth supra.

For purposes of the present invention, sequence identity to any of the promoter sequences disclosed herein is preferably made using art known methodologies such as the BLAST program, or any sequence alignment program that allows the alignment of identical nucleotides and verification of mismatches between non-identical nucleotides so that the percentage of identity of compared sequences could be estimated.

The cambium/xylem-preferred promoters of the invention may be used to express a gene of interest. For example, by using cambium/xylem-preferred promoters, the expression of native and/or non-native genes could be regulated in the cambium and/or xylem tissues of a plant, thus altering a plant's cellulose content, lignin content, pathogen or insect resistance, wood development, wood quality, and the like. The native and/or non-native genes include those encoding enzymes, transporters, cofactors, transcription factors and a number of other genes that would affect cellulose and/or lignin deposition in the plant or pathogen or insect resistance.

For the present invention, "genes of interest" include those involved in cellulose metabolism and lignin metabolism. It is recognized that any gene of interest can be operably linked to the promoter of the invention and expressed in plant cambium and/or xylem tissues.

The cambium/xylem-preferred promoters of the present invention, when operably linked to a gene of interest and stably incorporated into a plant genome, drive cambium and/or xylem-preferred expression of the said gene of interest. Cambium and/or xylem-preferred expression is intended to mean that expression of the gene of interest is most abundant in the cambium and/or in the xylem, although some level of expression of the gene of interest may occur in other plant tissues. Cambium encompasses any part of the cambial or procambial tissue in any organ of the plant, including but not being limited to the root, shoot, stem, wood, leaf, petiole, and the like. Xylem means any part of the xylem tissue, including but not being limited to the tracheids, tracheary elements, vessels, fuse fibers and pith. Some of the promoters disclosed herein may drive the expression of genes to the secondary xylem more prominently than to the primary xylem.

The constructs containing the cambium/xylem-preferred promoters disclosed in the present invention and an operably linked gene of interest may be provided in expression cassettes as depicted in the figures. Such expression cassettes comprise the cambium/xylem-preferred promoters of the present invention, or variants or fragments thereof, operably linked to a gene of interest whose expression is directed to the cambium and/or xylem. Such an expression cassette may contain restriction sites for insertion of the gene of interest under the transcriptional control of the cambium/xylem-preferred promoters. The expression cassette may additionally contain a number of other nucleic acid sequences, including selectable marker genes; transcriptional and translational initiation sequences, and a plant transcriptional and translational termination sequence. The termination region may be native with the DNA sequence of interest or may be from the Ti-plasmid of *A. tumefaciens*, such as the octopine synthase and nopaline synthase termination regions (Gielen et al., EMBO J., 3:835-846 (1984), Depicker et al., Mol. and Appl. Genet., 1:561-573 (1982)).

Reporter genes or selectable marker genes may be included in the expression cassettes. Examples of suitable reporter genes known in the art can be found in for example, Jefferson et al. (1991) in *Plant Molecular Biology Manual*, ed. Gelvin et al. (Kluwer Academic Publishers), pp. 1-33. Selectable marker genes for selection of transformed cells or tissues can include genes that confer herbicide resistance Examples of suitable selectable marker genes include, but are not limited to, genes encoding resistance to sulfonamide (Guerineau et al. (1990) *Plant Mol. Biol.* 15:127-136), bromoxynil (Stalker et al. (1988) *Science* 242:419-423), glyphosate (Shaw et al. (1986) *Science* 233:478-481) and phosphinothricin (De-Block et al. (1987) *EMBO J.* 6:2513-2518).

The expression cassettes of the present invention operably linked to a gene of interest are useful for the transformation of a variety of plants. Such plants, include, but are not limited to, *Eucalyptus* species (*E. alba, E. albens, E. amygdalina, E. aromaphloia, E. baileyana, E. balladoniensis, E. bicostata, E. botryoides, E. brachyandra, E. brassiana, E. brevistylis, E. brockwayi, E. camaldulensis, E. ceracea, E. cloeziana, E. coccifera, E. cordata, E. cornuta, E. corticosa, E. crebra, E. croajingolensis, E. curtisii, E. dalrympleana, E. deglupta, E. delegatensis, E. delicata, E. diversicolor, E. diversifolia, E. dives, E. dolichocarpa, E. dundasii, E. dunnii, E. elata, E. erythrocorys, E. erythrophloia, E. eudesmoides, E. falcata, E. gamophylla, E. glaucina, E. globulus, E. globulus* subsp. *bicostata, E. globulus* subsp. *globulus, E. gongylocarpa, E. grandis, E. grandis×urophylla, E. guilfoylei, E. gunnii, E. hallii, E. houseana, E. jacksonii, E. lansdowneana, E. latisinensis, E. leucophloia, E. leucoxylon, E. lockyeri, E. lucasii, E. maidenii, E. marginata, E. megacarpa, E. melliodora, E. michaeliana, E. microcorys, E. microtheca, E. muelleriana, E. nitens, E. nitida, E. obliqua, E. obtusiflora, E. occidentalis, E. optima, E. ovata, E. pachyphylla, E. pauciflora, E. pellita, E. perriniana, E. petiolaris, E. pilularis, E. piperita, E. platyphylla, E. polyanthemos, E. populnea, E. preissiana, E. pseudoglobulus, E. pulchella, E. radiata, E. radiata* subsp. *radiata, E. regnans, E. risdonii, E. robertsonii, E. rodwayi, E. rubida, E. rubiginosa, E. saligna, E. salmonophloia, E. scoparia, E. sieberi, E. spathulata, E. staeri, E. stoatei, E. tenuipes, E. tenuiramis, E. tereticornis, E. tetragona, E. tetrodonta, E. tindaliae, E. torquata, E. umbra, E. urophylla, E. vernicosa, E. viminalis, E. wandoo, E. wetarensis, E. willisii, E. willisii* subsp. *falciformis, E. willisii* subsp. *willisii, E. woodwardii*), *Populus* species (*P. alba, P. alba×P. grandidentata, P. alba×P. tremula, P. alba×P. tremula* var. *glandulosa, P. alba×P. tremuloides, P. balsamifera, P. balsamifera* subsp. *trichocarpa, P. balsamifera* subsp. *trichocarpa×P. deltoides, P. ciliata, P. deltoides, P. euphratica, P. euramericana, P. kitakamiensis, P. lasiocarpa, P. laurifolia, P. maximowiczii, P. maximowiczii×P. balsamifera* subsp. *trichocarpa, P. nigra, P. sieboldii×P. grandidentata, P. suaveolens; P. szechuanica, P. tomentosa, P. tremula, P. tremula×P. tremuloides, P. tremuloides, P. wilsonii, P. canadensis, P. yunnanensis*) and Conifers as, for example, loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The expression cassettes may be stably incorporated into plant genomes by *Agrobacterium*-mediated transformation (Fraley et al. (1983) *Proc. Natl. Acad. Sci. USA.* 80:4803-4807) or by the biobalistics method (Klein et al. (1987) *Nature.* 327:70-73).

All technical terms used herein are terms commonly used in biochemistry, molecular biology and agriculture, and can be understood by one of ordinary skill in the art to which this invention belongs. Those technical terms can be found in: Molecular Cloning: A Laboratory Manual, 3rd ed., vol. 1-3, ed. Sambrook and Russel, Cold Spring Harbor Laboratory Press, Cold Spring Harbor, N.Y., 2001; Current Protocols in Molecular Biology, ed. Ausubel et al., Greene Publishing Associates and Wiley-Interscience, New York, 1988 (with periodic updates); Short Protocols in Molecular Biology: A Compendium of Methods from Current Protocols in Molecular Biology, 5$^{th}$ ed., vol. 1-2, ed. Ausubel et al., John Wiley & Sons, Inc., 2002; Genome Analysis: A Laboratory Manual, vol. 1-2, ed. Green et al., Cold Spring Harbor Laboratory Press, Cold Spring Harbor, N.Y., 1997. Methods involving plant biology techniques are described herein and are described in detail in methodology treatises such as Methods in Plant Molecular Biology: A Laboratory Course Manual, ed. Maliga et al., Cold Spring Harbor Laboratory Press, Cold Spring Harbor, N.Y., 1995. Various techniques using PCR are described, e.g., in Innis et al., PCR Protocols: A Guide to Methods and Applications, Academic Press, San Diego, 1990 and in Dieffenbach and Dveksler, PCR Primer: A Laboratory Manual, 2$^{nd}$ ed., Cold Spring Harbor Laboratory Press, Cold Spring Harbor, N.Y., 2003. PCR-primer pairs can be derived from known sequences by using computer programs intended for that purpose (e.g., Primer, Version 0.5, 1991, Whitehead Institute for Biomedical Research, Cambridge, Mass.). Methods for chemical synthesis of nucleic acids are discussed, for example, in Beaucage and Caruthers (1981) Tetra. Lett. 22:1859-1862 and Matteucci and Caruthers (1981) J. Am. Chem. Soc. 103:3185.

The present invention is further illustrated by the following specific examples. The examples are provided for illustration only and are not to be construed as limiting the scope or content of the invention in any way.

Example 1

Expression Profile of Genes Preferably Expressed in Cambium/Xylem

Expressed Sequence Tags (ESTs) from *Populus* sp. were clustered using the CAP3 program (Huang and Madan (1999) *Genome Res.* 9:868-877). Such ESTs were obtained from libraries representing the following tissues: apical shoot, bark, cambium, seed, xylem, leaf and root. The set of clusters thus generated was searched for those clusters composed of at least 90% of ESTs from libraries representing *Populus* cambium and xylem tissues. Twelve clusters were chosen based on their high and preferred level of expression in the cambium and/or in the xylem of *Populus*. A BLASTX search against the non-redundant GenBank database was then performed with each one of the twelve clusters, and it was concluded that they represent expressed sequences from the following genes, sucrose synthase (SuSy), alpha-tubulin (TUB), arabinogalactan protein (ARAB), caffeic acid 3-O-methyltransferase (COMT), cinnamyl alcohol dehydrogenase (CAD), cinnamate 4-hydroxylase (C4H), cinnamoyl CoA reductase (CCR), ferulate-5-hydroxylase (F5H), sinapyl alcohol dehydrogenase (SAD), UDP-D-glucuronate carboxy-lyase (UDP), lipid transfer protein (LTP) and ag-13 (AG13). FIGS. 2 and 3 show the expression profile in several tissues of *Populus* for each of the clusters representing the genes whose promoters are disclosed herein. The series of histograms in FIGS. 2 and 3 ultimately depict the relative abundance of each gene in cDNA libraries representing the aforementioned tissues (apical shoot, bark; cambium, seed, xylem, leaf and root). Thus, the histograms compose a set of digital expression data which is an approximation of the relative level of expression for the twelve genes whose promoters are disclosed herein.

Example 2

Isolation of Promoter Sequences

BLASTN was performed for each one of the twelve clusters against the genomic sequences from *Populus trichocarpa* made available by the Joint Genome Institute, US Department of Energy as part of the "*Populus* Genome Sequencing Project" (genome.jgi-psf.org/poplar0/poplar0.info.html). Selected nucleotide regions from each cluster corresponding to putative exons were used as driver sequences in the retrieval of genomic sequence reads comprising the transcription initiation region and adjacent upstream promoter sequences. These genomic reads were assembled using the PHRAP (Gordon et al. (1998) *Genome Res.* 8:195-202) program to obtain a contig encompassing approximately 700 to 3500 nucleotides of putative promoter region upstream from the transcription initiation point (+1 nucleotide, which corresponds to the beginning of the respective mRNA). These contigs contain the promoter regions for each of the genes encoding the mRNAs represented by the twelve clusters concluded to be preferably expressed in the cambium and/or in the xylem tissues of *Populus*. These twelve promoter regions correspond to sequences disclosed herein under SEQ ID NOS.: 1-12.

For isolation of specific promoter regions, pairs of gene-specific primers (usually 30 nt in length) were designed from the sequences of the promoter contigs described above to amplify by PCR a fragment of 700 to 3500 nucleotides from the promoter region of each one of the twelve genes whose promoter sequences are disclosed herein. The first round of PCR was performed on genomic DNA sample from *Populus deltoides* or *P. trichocharpa*, which was prepared from leaves using the cetyltrimethyl-ammonium bromide (CTAB) extraction method (Aldrich and Cullis (1993) *Plant Mol. Biol. Report*. 11:128-141). The primers were designed to amplify the region upstream of the coding sequence, i.e., the 5' untranslated region and promoter region of the chosen gene. The sequences of the primers used are given below for each promoter:

```
sucrose synthase (SuSy)
5'-GCCATAGCTCCTTAAGAGAAACAGAAAGCAA-3'      (SEQ ID NO: 13)
5'-CAATATAGAATCAATGAACAGCACTAGTTTGC-3'     (SEQ ID NO: 14)
5'-TCATGTCCTATCCAACGGCG-3'                 (SEQ ID NO: 15)

alpha-tubulin (TUB)
5'-CTCATTTTCTCTCAAAGCTCAAAG-3'             (SEQ ID NO: 16)
5'-GACAACTAGTCTAAAGTTAAAACTTAGACC-3'       (SEQ ID NO: 17)
5'-CCCTGGAGGTTGGGGTGAGT-3'                 (SEQ ID NO: 18)

arabinogalactan protein (ARAB)
5'-GCGTTCATCTACAAAACCCTCCTCC-3'            (SEQ ID NO: 19)
5'-TTCATCCTTATTTTTTTGGGATA-3'              (SEQ ID NO: 20)
5'-CAAAGGATCATGGAGTTGGA-3'                 (SEQ ID NO: 21)
```

-continued

```
caffeic acid 3-O-methyltransferase (COMT)
5'-TATACTAATATGACCTAATAACTTAGAAGTGTGG-3'    (SEQ ID NO: 22)
5'-CATCTTGATCAAGATTGAATTC-3'                (SEQ ID NO: 23)
5'-CATAATATCAAAACTTAAGC-3'                  (SEQ ID NO: 24)

cinnamyl alcohol dehydrogenase (CAD)
5'-TGAATTGATGACGTAGGAAACATGATAAACATG-3'     (SEQ ID NO: 25)
5'-CATTTTCTTGAAACAATGAGGCTAAGAG-3'          (SEQ ID NO: 26)

cinnamate 4-hydroxylase (C4H)
5'-GACATGAGAAACTAACGTTGCTTGAATTC-3'         (SEQ ID NO: 27)
5'-CATAATATTGGAACTGGTTTCTTTGTCAGAAAG-3'     (SEQ ID NO: 28)

cinnamoyl CoA reductase (CCR)
5'-GCGCTCGGGTTGTCACCATAGTTTC-3'             (SEQ ID NO: 29)
5'-CATGTTGTTATATTTAGATAAATGTA-3'            (SEQ ID NO: 30)

ferulate-5-hydroxylase (F5H)
5'-TTCATCAAGCAATAATAATAAGGTGAGGC-3'         (SEQ ID NO: 31)
5'-CATGGATGCAGATTTTTGTGTTTGTG-3'            (SEQ ID NO: 32)
5'-TTCAGTGAACATGCTGCCACAATGAC-3'            (SEQ ID NO: 33)

sinapyl alcohol dehydrogenase (SAD)
5'-AATCGAAACCGATCGATTTGAACTGG-3'            (SEQ ID NO: 34)
5'-CATGGTGCTTGCTTCAGATAG-3'                 (SEQ ID NO: 35)

UDP-D-glucuronate carboxy-lyase (UDP)
5'-GGAAATGTCAACACTTGTGTGACCACAC-3'          (SEQ ID NO: 36)
5'-GACATTCTTGTCCAATTTCTGAA-3'               (SEQ ID NO: 37)

lipid transfer protein (LTP)
5'-GGAGCCTCCATATTTCTGTATCTC-3'              (SEQ ID NO: 38)
5'-CAAGACGATGAAATGAAGAACTGATAGC-3'          (SEQ ID NO: 39)

ag-13 (AG13)
5'-GACATTCCTTGACTTAATATGATGCT-3'            (SEQ ID NO: 40)
5'-GAATTCGCATCCATGCGGTGAGTTCG-3'            (SEQ ID NO: 41)
```

Figure 4:
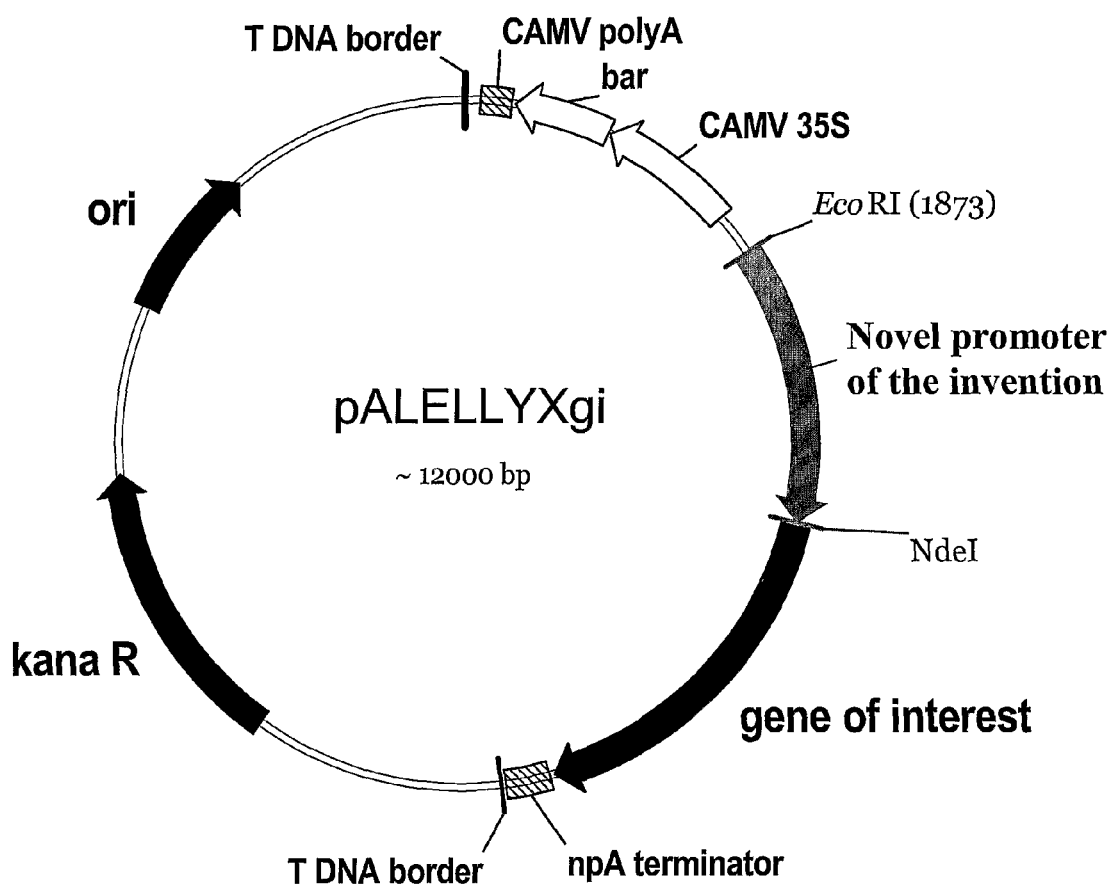
FIG. 4 schematically illustrates the plasmid vector pALELLYXgi which is another embodiment of the invention.

PCR was performed using commercially available reagents and cycle parameters of 5 min at 94° C. followed by 35 cycles of 94° C. for 1 min, then a varying annealing temperature, as described infra for 1 min, then 72° C. for 3 min. The annealing temperature (T) was adjusted for each primer pair and ranged from 50° C. to 59° C. Finally, the samples were held at 72° C. for 7 min, then at 4° C. until further analysis. Ten μl of each of the resulting amplified DNA fragments were run on a 0.8% agarose gel, purified using the GFX Gel Purification Kit (Amersham), subcloned into pGEM-T-Easy vector (Promega) and then into EcoRI and BglII sites of the pAPROM-ATG vector. Final sequences were determined on the resulting plasmids. FIG. 1 schematically illustrates the expression cassette pAPROM-ATG comprising the GUS gene operably linked to a promoter disclosed herein. FIG. 4 schematically illustrates the plasmid vector comprising a gene of interest operably linked to a promoter of the invention.

Example 3

Transformation of *Arabidopsis* Plants

*Arabidopsis thaliana* Columbia plants were transformed using an *Agrobacterium tumefaciens* mediated transformation protocol (Bechtold et al, (1993) C. R. *Acad. Sci. Paris* 316:1194-1199; Bent et al., (1986) *Mol. Gen. Genet.* 204: 383-396) with individual constructs containing any one of the promoters of the invention operably linked to a gene of interest. The constructs also contained the selectable marker gene Bar that confers resistance to herbicidal phosphinothricin analogs like ammonium gluphosinate (Thompson et al. (1987) *EMBO J.* 9:2519-2523). In this example, the gene of interest operably linked to the cambium/xylem-preferred promoters of the invention is the reporter gene Gus encoding the enzyme beta-glucuronidase (GUS) (Jefferson (1987) *Plant Mol. Biol. Rep.* 5: 387-405) that facilitates visual inspection of the desirable phenotype, i.e., expression of GUS in a cambium/xylem-preferred manner.

Seeds of *Arabidopsis thaliana* ecotype Columbia were sown in pots containing vermiculite. Plants were grown under a 16/8 hours dark/light regime at 22° C. After 4-5 weeks, plants were transformed with the *Agrobacterium tumefaciens* strain GV3101 in accordance with Bent et al., (1986) *Mol. Gen. Genet.* 204:383-396; which harbors the plasmid vector comprising the gene of interest operably linked to each one of the promoters of the invention.

For plant transformation, 1 liter of LB medium containing rifampicin, gentamycin and kanamicin was inoculated with an aliquot of overnight starter *Agrobacterium* culture. The culture was then grown overnight at 28° C. in a rotary shaker, until OD600 is ≥8.0. The *Agrobacterium* was precipitated by centrifugation and the bacterial pellet was resuspended in 300 ml of 5% sucrose and 0.03% Silwet L-77. This *Agrobacterium* suspension was sprayed onto the plants. The pots were placed in a tray which was covered with plastic wrap to maintain humidity and the plants were grown at the above regime, in order to mature and to set seeds.

Seeds were harvested and surface sterilized in a solution containing 50% bleach and 0.02% Triton X-100 for 7 minutes. Seeds were then rinsed 3 times in sterile distilled water and plated out in MS medium containing 6 mg/l of Finale as a selection agent. After 5 to 7 days, transformants were visible as green plants. Transformed plants were transferred onto new selection plates and after 6-10 days were transferred to pots containing vermiculite and grown under conditions of 16 hours light/8 hours dark at 22° C.

Example 4

GUS Expression Assay in *Arabidopsis* Plants

Inflorescence stems of the transformed plants described in EXAMPLE 3 were cut and histologically stained for GUS activity. Subsequent cuttings induced the formation of secondary xylem at the basis of plants that could also be histologically stained for GUS activity.

Figure 5:
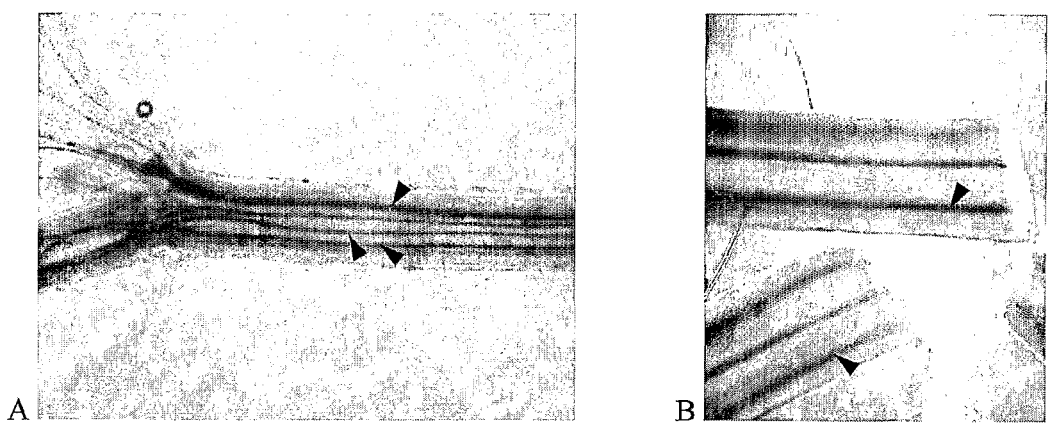
FIGS. 5A and 5B show beta glucoronidase activity in the flowering stem of *Arabidopsis* plants, transformed in accordance with Example 3.

In FIGS. 5A and 5B, activity of beta-glucuronidase in flowering stems of transgenic *Arabidopsis* plants is shown. These transgenic *Arabidopsis* plants were transformed with a construct containing the gene Gus operably linked to cambium/xylem-preferred promoters of the invention, namely TUB (SEQ ID.: 2) (A) and C4H (SEQ ID.: 6) (B). Darker bands along the longitudinal axis of the stem (arrowheads) represent primary vascular bundles stained blue after the chromogenic assay, indicating the functionality and tissue-specificity of the respective promoter in each transgenic line.

The table below summarizes GUS assay data obtained through the analysis of inflorescence stem cuttings of *Arabidopsis thaliana* plants transformed with expression constructs according to EXAMPLE 2 comprising the Gus gene under the control of promoter sequences disclosed herein. For all promoters tested, vascular GUS expression pattern was observed. In some cases, GUS activity was markedly high in specific vascular cell types such as vessel elements, as for example in plants transformed with constructs comprising the LTP (SEQ ID.: 11), C4H (SEQ ID.: 6) or TUB (SEQ ID.: 2) promoters. In other cases, a vascular pattern was observed but no specific cell type therein could be pinpointed as the main GUS expression site.

| | | | Expression pattern | | |
|---|---|---|---|---|---|
| Promoter | No. of events analyzed | Total of GUS-positive events | Vessel elements only | Vessel elements + other vascular cell types | Non-vascular cell types |
| SUSY | 92 | 21 | 1 | 17 | 3 |
| LTP | 75 | 38 | 19 | 14 | 5 |
| C4H | 89 | 43 | 14 | 28 | 1 |
| TUB | 78 | 20 | 9 | 10 | 1 |
| COMT | 72 | 24 | 2 | 15 | 7 |
| CAD | 79 | 37 | 8 | 16 | 13 |
| SAD | 75 | 30 | 4 | 13 | 13 |
| UDP | 72 | 20 | 4 | 14 | 2 |
| CCR | 74 | 22 | 4 | 14 | 4 |

Other aspects of the invention will be clear to the skilled artisan, and need not be reiterated here.

The terms and expression which have been employed are used as terms of description and not of limitation, and there is no intention in the use of such terms and expression of excluding any equivalents of the features shown and described or portions thereof, it being recognized that various modifications are possible with the scope of the invention.

What is claimed is:

1. An expression vector comprising: (i) an isolated nucleic acid molecule comprising a nucleotide sequence that is capable of initiating transcription of a gene in a plant cell, wherein said isolated nucleic acid molecule consists of the nucleotide sequence set forth in SEQ ID NO: 2 and (ii) a nucleic acid molecule which encodes a protein of interest, wherein (i) and (ii) are in operable linkage, wherein (i) is heterologous to (ii).

2. The expression vector of claim 1, wherein said expression vector is a plasmid.

3. A recombinant plant cell, wherein said recombinant plant cell is transformed or transfected with an isolated nucleic acid molecule consisting of the nucleotide sequence set forth in SEQ ID NO: 2; and functions as a cambium/xylem-preferred promoter for a Populus gene encoding alpha-tubulin expression.

4. A recombinant plant cell, wherein said recombinant plant cell is transformed or transfected with the expression vector of claim 1.

5. The recombinant plant cell of claim 3, wherein said isolated nucleic acid molecule is stably incorporated in said recombinant plant cell's genome.

6. The recombinant plant cell of claim 4, wherein said expression vector is stably incorporated in said recombinant plant cell's genome.

7. A method of making a recombinant host cell, said method comprising transforming or transfecting a cell with the expression vector of claim 1.

8. A method of making a protein encoded by the expression vector of claim 1, comprising transforming or transfecting a cell with said expression vector, and culturing said cell under conditions favorable for the expression of said protein.

9. The method of claim 7, wherein said recombinant host cell is a plant cell.

10. A method for making a protein, said method comprising culturing a plant or plant part which comprises a recombinant host cell transformed or transfected with the expression vector of claim 1, under conditions favoring production of said protein by said plant or plant part.

11. The method of claim 10, wherein said plant is a dicot.

12. The method of claim 11, wherein said dicot is *Eucalyptus*.

13. The method of claim 11, wherein said dicot is *Populus*.

14. The method of claim 10, wherein said plant is a monocot.

15. The method of claim 10, wherein said plant is a gymnosperm.

16. The method of claim 15, wherein said gymnosperm is *Pinus*.

17. A plant or plant part comprising the recombinant plant cell of claim 3.

18. The plant of claim 17, wherein said plant is a dicot.

19. The plant of claim 18, wherein said dicot is *Eucalyptus*.

20. The plant of claim 18, wherein said dicot is *Populus*.

21. The plant of claim 17, wherein said plant is a monocot.

22. The plant of claim 17, wherein said plant is a gymnosperm.

23. The plant of claim 22, wherein said gymnosperm is *Pinus*.

24. The plant part of claim 17, wherein said plant part is a seed.

25. The recombinant plant cell of claim 3, wherein said recombinant plant cell is a pollen cell.

26. The method of claim 10, wherein said plant part is selected from the group consisting of a root, a stem, a leaf, a flower, a fruit, a seed, a pistil, a stigma, a style, an ovary, an ovule, an stamen, an anther, and an filament.

* * * * *